United States Patent
Tanimoto et al.

(10) Patent No.: US 8,396,722 B2
(45) Date of Patent: Mar. 12, 2013

(54) MEDICINE EXAMINATION SUPPORT SYSTEM

(75) Inventors: Takanobu Tanimoto, Osaka (JP); Makoto Gotou, Hyogo (JP); Yoshihiko Matsukawa, Nara (JP); Tohru Nakamura, Osaka (JP); Rie Takahashi, Osaka (JP)

(73) Assignee: Panasonic Corporation, Osaka (JP)

( * ) Notice: Subject to any disclaimer, the term of this patent is extended or adjusted under 35 U.S.C. 154(b) by 321 days.

(21) Appl. No.: 12/995,470

(22) PCT Filed: Mar. 24, 2010

(86) PCT No.: PCT/JP2010/002045
§ 371 (c)(1),
(2), (4) Date: Dec. 1, 2010

(87) PCT Pub. No.: WO2010/113421
PCT Pub. Date: Oct. 7, 2010

(65) Prior Publication Data
US 2011/0125523 A1    May 26, 2011

(30) Foreign Application Priority Data

Mar. 31, 2009  (JP) .................................. 2009-084547

(51) Int. Cl.
*G06Q 10/00*  (2012.01)
(52) U.S. Cl. .................. 705/2; 705/3; 705/308; 705/28; 715/236; 209/702
(58) Field of Classification Search .................. 705/2, 3, 705/28

See application file for complete search history.

(56) References Cited

U.S. PATENT DOCUMENTS

| 7,349,858 | B1* | 3/2008 | McGrady et al. | 705/3 |
| 7,395,214 | B2* | 7/2008 | Shillingburg | 705/2 |
| 7,467,093 | B1* | 12/2008 | Newton et al. | 705/3 |
| 7,685,026 | B1* | 3/2010 | McGrady et al. | 705/28 |
| 2007/0208598 | A1* | 9/2007 | McGrady et al. | 705/3 |
| 2008/0149656 | A1 | 6/2008 | Yuyama et al. | |

FOREIGN PATENT DOCUMENTS

| JP | 2005-046420 | 2/2005 |
| JP | 2006-247150 | 9/2006 |
| JP | 2008-112231 | 5/2008 |
| WO | 2006/046642 | 5/2006 |

OTHER PUBLICATIONS

Google patents search, Dec. 10, 2012.*
ProQuest search, Dec. 10, 2012.*
International Search Report issued Jun. 22, 2010 in International (PCT) Application No. PCT/JP2010/002045.

* cited by examiner

*Primary Examiner* — Dilek B Cobanoglu
(74) *Attorney, Agent, or Firm* — Wenderoth, Lind & Ponack LLP.

(57) ABSTRACT

A medicine inspection support system, which provides a reliable inspection of medicine preparation, includes a person authentication unit, a preliminary inspection unit, an inspection unit, and an inspector check unit. The person authentication unit identifies a preliminary inspector who performs a preliminary inspection of medicine preparation, and an inspector who performs an inspection of the medicine preparation. The preliminary inspection unit certifies that the preliminary inspector has performed the preliminary inspection of the medicine preparation. The inspection unit certifies that the inspector has performed the inspection of the medicine preparation. The inspector check unit permits the inspection unit to certify completion of the inspection when determined that the inspector is a different person from the preliminary inspector.

13 Claims, 23 Drawing Sheets

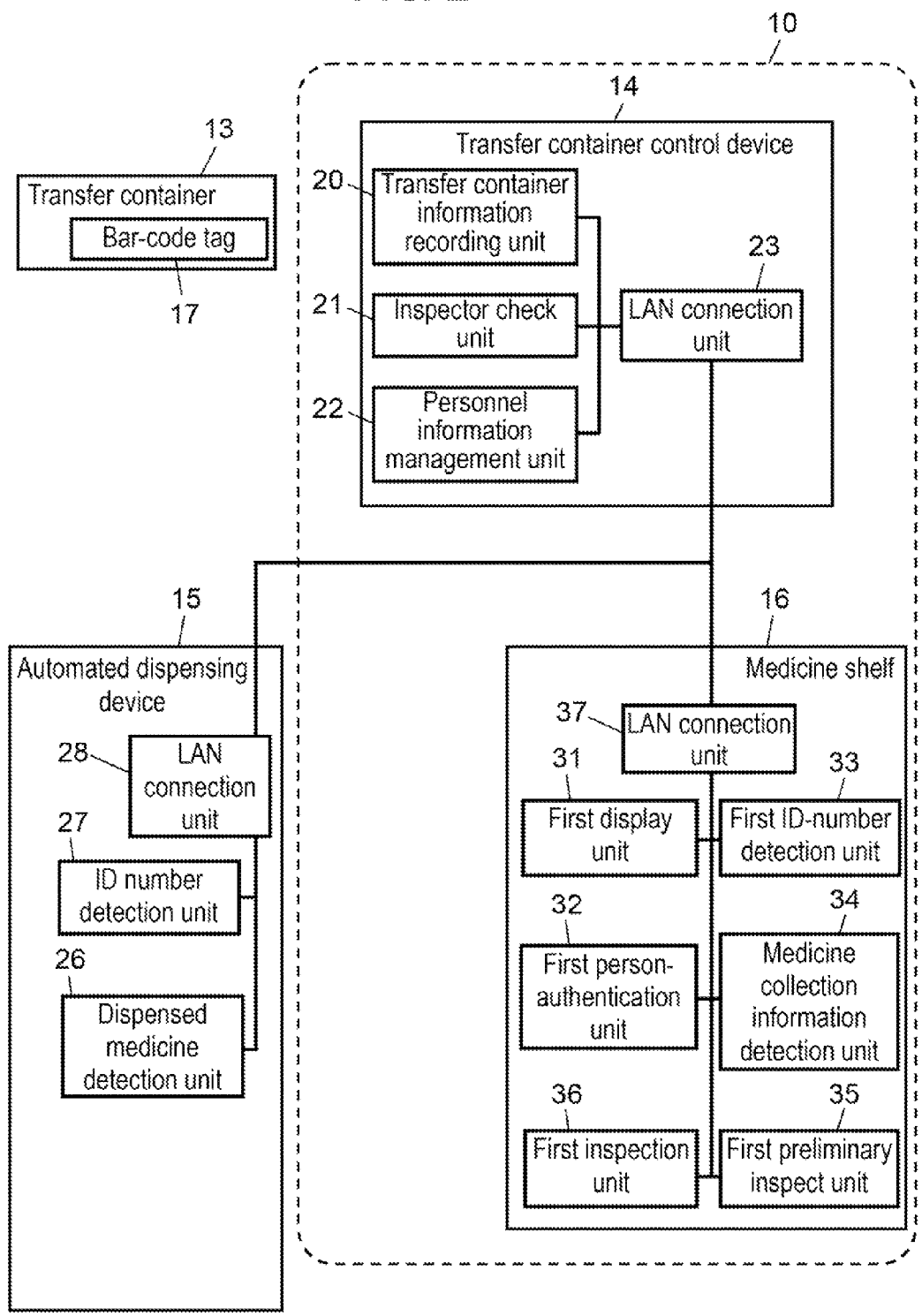

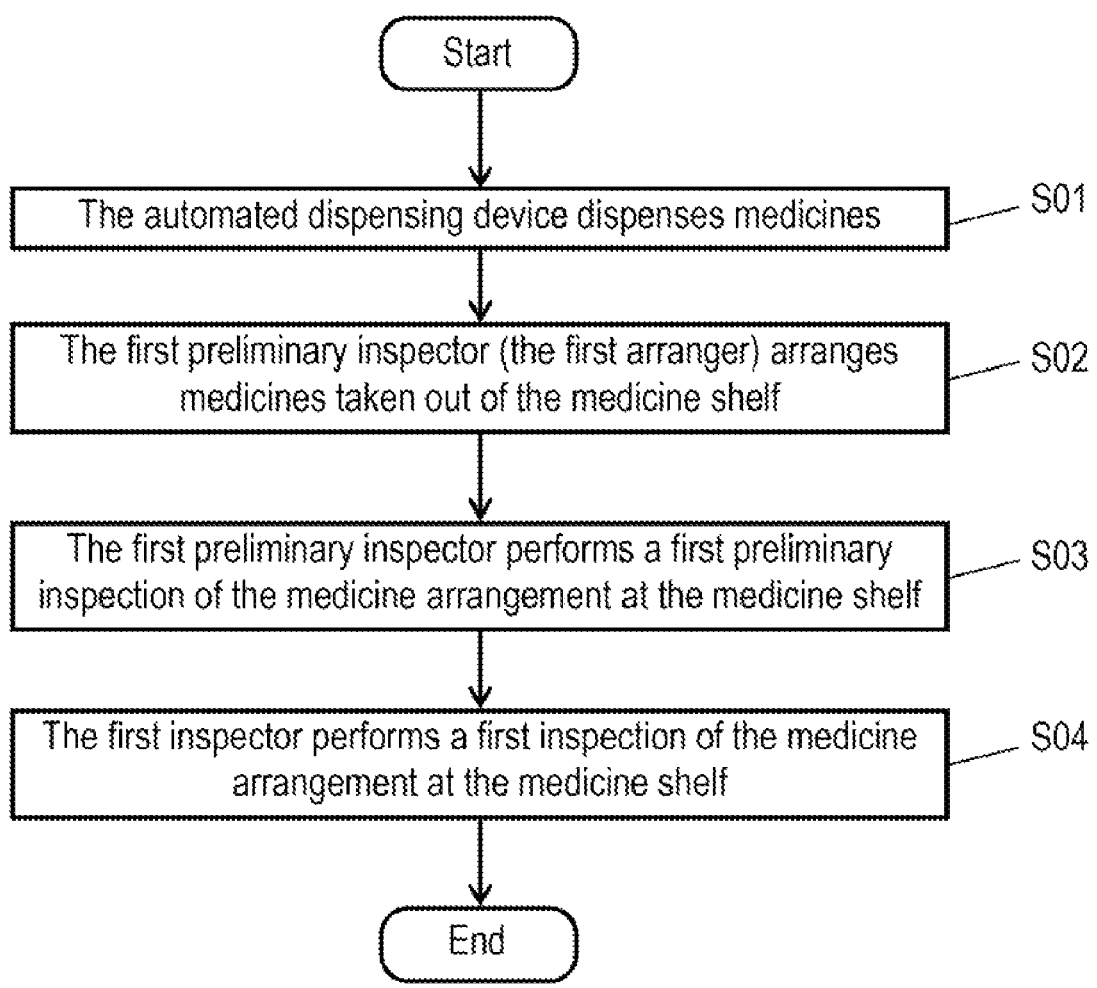

FIG.4

| Transfer container ID number | Prescription information | Information about medicines from dispensing device | Information about medicines from medicine shelf | First preliminary inspection | First inspection |
|---|---|---|---|---|---|
| 0003 | MORNING Medicine A (1), Medicine C (1), Medicine D (1) EVENING Medicine A (1), Medicine C (1) | MORNING Medicine A (1) EVENING Medicine A (1) | MORNING Medicine C (1) EVENING Medicine C (1) | First medicine-arranger | First operator |
| 0004 | MORNING Medicine A (1), Medicine C (1), Medicine D (1) NOON Medicine A (1), Medicine B (2) EVENING Medicine A (1), Medicine C (1) | MORNING Medicine A (1) NOON Medicine A (1), Medicine B (2) EVENING Medicine A (1) | | | |

FIG. 18

| Transfer container ID number | Prescription information | Information about medicines from dispensing device | Information about medicines from medicine shelf | First preliminary inspection | First inspection | Information about medicines from medicine cabinet | Second preliminary inspection | Second inspect |
|---|---|---|---|---|---|---|---|---|
| 0003 | MORNING Medicine A (1), Medicine C (1), Medicine D (1) EVENING Medicine A (1), Medicine C (1) | MORNING Medicine A (1) EVENING Medicine A (1) | MORNING Medicine C (1) EVENING Medicine C (1) | First medicine-arranger | First operator | MORNING Medicine D (1) | Second medicine-arranger | Second operator |
| 0004 | MORNING Medicine A (1), Medicine C (1), Medicine D (1) NOON Medicine A (1), Medicine B (2) EVENING Medicine A (1), Medicine C (1) | MORNING Medicine A (1) NOON Medicine A (1), Medicine B (2) EVENING Medicine A (1) | | | | | | |

FIG. 23

| Transfer container ID number | Prescription information | Information about medicines from dispensing device | Information about medicines from medicine shelf | First preliminary inspection | First Inspection | First operation certification time | Information about medicines from medicine cabinet | First preliminary inspection | Second inspection | Second operation certification time |
|---|---|---|---|---|---|---|---|---|---|---|
| 0003 | MORNING Medicine A (1), Medicine C (1), Medicine D (1) EVENING Medicine A (1), Medicine C (1) | MORNING Medicine A (1) EVENING Medicine A (1) | MORNING Medicine C (1) EVENING Medicine C (1) | First medicine-arranger | First operator | 13:03 | MORNING Medicine D (1) | Second medicine-arranger | Second operator | 13:26 |
| 0004 | MORNING Medicine A (1), Medicine C (1), Medicine D (1) NOON Medicine B (2) EVENING Medicine A (1), Medicine C (1) | MORNING Medicine A (1), NOON Medicine B (2) EVENING Medicine A (1) | MORNING Medicine C (1) EVENING Medicine C (1) | First medicine-arranger | First operator | 15:44 | MORNING Medicine D (1) | Second medicine-arranger | Second operator | |

74

MEDICINE EXAMINATION SUPPORT SYSTEM

TECHNICAL FIELD

The invention relates to a medicine inspection support system for supporting an inspection of the preparation of medicines to be administered to patients.

BACKGROUND ART

Medicines to be administered to hospital inpatients are determined based on prescriptions from doctors, and arranged in transfer containers such as trays and envelops by pharmacists according to the prescriptions. Most of these medicines are automatically dispensed by an automated dispensing device.

There are, on the other hand, some medicines under supervised conditions that are required to be treated by pharmacists and are not permitted to be dispensed by automated dispensing devices. Thus, human work cannot be completely removed from medicine arrangement.

However, such manual work may result in incorrect medicine arrangement due to human error. Therefore, to provide more reliable medicine arrangement, an attempt has been made to direct pharmacists which medicines to be arranged by using LED illumination (see, for example, Patent Literature 1).

The following is a description, with reference to FIG. 24, of conventional medicine arrangement support system 1. In FIG. 24, first of all, transfer container 3 is transferred to workbench 2 of system 1. Next, medicine arranger 4 scans the ID number of the transfer container with a bar-code reader or other similar device. As a result, the name of the patient and his/her prescription are displayed on display unit 5 based on the ID number. Watching the display, medicine arranger 4 arranges medicines that are not dispensed by automated medicine dispensing device 6. At this moment, the LEDs of the medicine storage compartments in medicine shelf 7 light up, indicating which compartments contain the medicines to be arranged. Thus, system 1 instructs medicine arranger 4 which medicines to be arranged by using LED illumination, thereby supporting medicine arrangement.

Medicine arranger 4 takes a necessary number of medicines out of the compartments with illuminating LEDs in medicine shelf 7. With the knowledge of the precise locations of the compartments containing the necessary medicines, medicine arranger 4 can arrange medicines correctly, which indicates high reliability of medicine arrangement.

When the arrangement of the necessary medicines is completed, medicine arranger 4 inspects as to whether the medicine arrangement has been done correctly by referring to the prescription displayed on display unit 5.

In order to prevent human error, an inspector, who is a different person from medicine arranger 4, inspects as to whether medicine arranger 4 has arranged medicines correctly in transfer container 3 according to a prescription.

Medicine arrangement is inspected as described hereinbefore. In some hospitals, there is, besides medicine shelf 7, a medicine cabinet (not shown) for infusion bags and other materials that should be kept under controlled temperature. In the case where both shelf 7 and the cabinet are used, medicines from shelf 7 are inspected first, and then infusion bags that are not contained in shelf 7 are dispensed from the cabinet, and inspected at the cabinet.

In the conventional medicine arrangement support system 1, it is determined that an inspector who performs an inspect should be a different person from medicine arranger 4. Actually, however, the role of the inspector is sometimes played by medicine arranger 4. This is because some hospitals with a shortage of workers have no other choice but to have the same person sometimes act as both medicine arranger 4 and an inspector.

Inspectors may make mistakes in an inspection of medicine arrangement, due for example to the lack of concentration or to the influence of preceding prescriptions when inspectors inspect different medicine arrangements in succession.

Thus, a human-performed inspection of medicine arrangement involves human error.

This can also happen when the same person performs an inspection at different locations. For example, when the same inspector performs an inspection at both the shelf and the cabinet, the inspection results at the shelf may confuse the inspector's thought process while inspecting at the cabinet. This may result in incorrect inspection results due to human error.

In order to prevent such human error so as to provide more reliable medicine preparation, it is preferable to perform a double inspect by two persons.

In the conventional medicine inspection support system, however, medicine preparation is often inspected by one inspector against the rule that the medicine preparation should be inspected by two inspectors to improve reliability. This may result in human error, making the inspection of the medicine preparation less reliable. Thus, the problem of the conventional medicine inspection support system is that the inspecting rules designed to provide a reliable inspection are not followed in the medicine preparation.

PRIOR ART LIST

Patent Literature 1: Japanese Patent Unexamined Publication No. 2005-46420

SUMMARY OF THE INVENTION

To solve the above-described problem, the invention provides a medicine inspection support system for supporting a reliable inspection of medicine preparation.

The medicine inspection support system of the invention, which certifies that medicine preparation has been inspected by an inspection unit, thereby providing a reliable inspection of medicine preparation, includes a person authentication unit, a preliminary inspection unit, an inspection unit, and an inspector check unit. The person authentication unit identifies a preliminary inspector who performs a preliminary inspection of medicine preparation, and an inspector who performs an inspection of the medicine preparation. The preliminary inspection unit certifies that the preliminary inspector has performed the preliminary inspection of the medicine preparation. The inspection unit certifies that the inspector has performed the inspection of the medicine preparation. The inspector check unit permits the inspection unit to certify completion of the inspection when determined that the inspector is a different person from the preliminary inspector.

BRIEF DESCRIPTION OF THE DRAWINGS

FIG. 2 is a block diagram of the medicine inspection support system according to the first embodiment of the invention.

FIG. 3 is a flowchart of a medicine inspection support process according to the first embodiment of the invention.

FIG. 4 shows a transfer container management table when some medicines are dispensed from an automated dispensing device according to the first embodiment of the invention.

FIG. 18 shows a transfer container management table according to the fourth embodiment of the invention.

FIG. 23 shows a transfer container management table according to the fifth embodiment of the invention.

DESCRIPTION OF EMBODIMENTS

Figure 1:
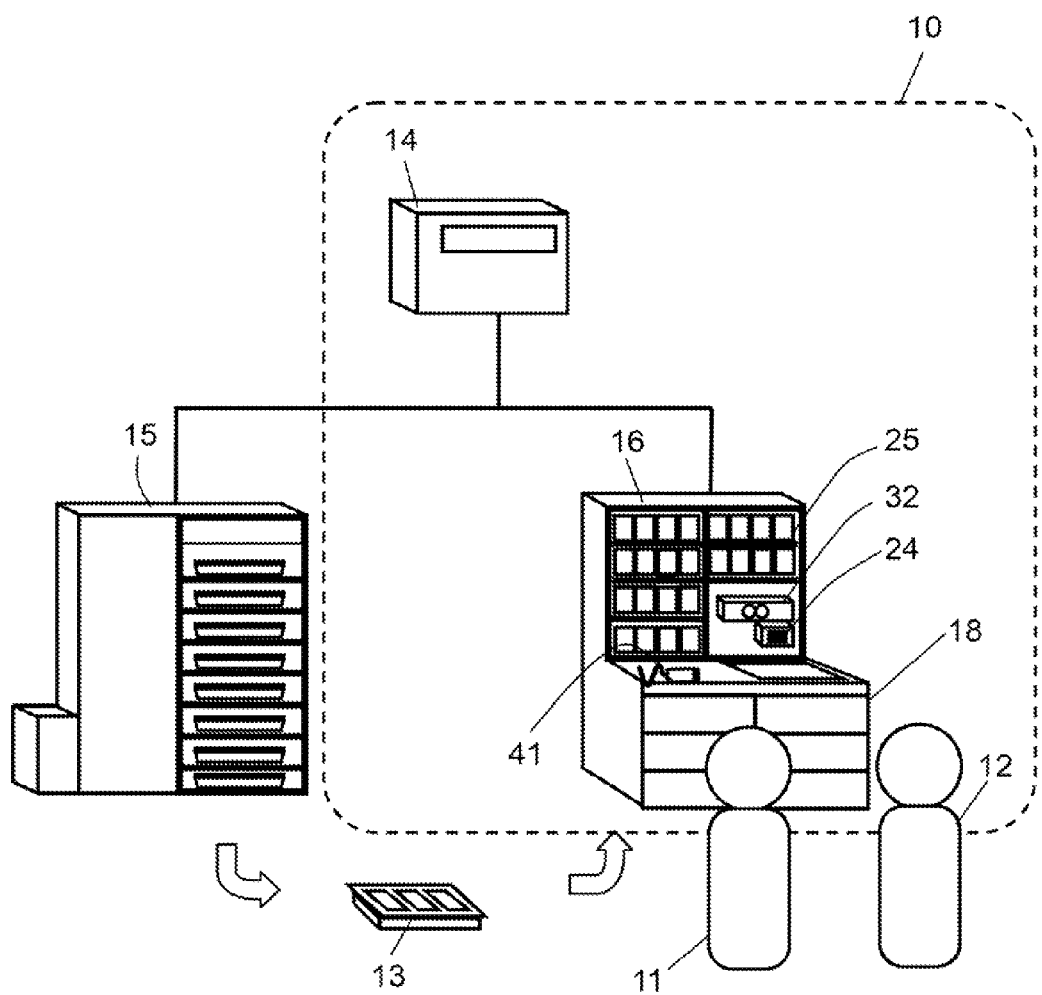
FIG. 1 is a schematic configuration view of a medicine inspection support system according to a first embodiment of the invention.

Embodiments of the invention will be described as follows with reference to drawings. In the second to fifth embodiments, like components are labeled with like reference numerals with respect to the preceding embodiments, and hence, the description thereof will be omitted.

First Embodiment

FIG. 1 is a schematic configuration view of medicine inspection support system 10 of a first embodiment of the invention. FIG. 2 is a block diagram of system 10.

As shown in FIGS. 1 and 2, medicine inspection support system 10 includes first person-authentication unit 32, first preliminary inspection unit 35, first inspection unit 36, and inspector check unit 21. First person-authentication unit 32 identifies first preliminary inspector 11 who performs a preliminary inspection of medicine preparation and first inspector 12 who performs an inspection of the medicine preparation. First preliminary inspection unit 35 certifies that first preliminary inspector 11 has performed the preliminary inspection of the medicine preparation. First inspection unit 36 certifies that first inspector 12 has performed the inspection of the medicine preparation.

Inspector check unit 21 determines whether first inspector 12 is a different person from first preliminary inspector 11, and when the determination is affirmative, permits first inspection unit 36 to certify completion of the inspection.

When having determined that inspectors 11 and 12 are the same person, on the other hand, inspector check unit 21 does not permit first inspection unit 36 to certify completion of the inspection. Thus, double inspecting requires that inspectors 11 and 12 be different persons. By doing so, medicine inspection support system 10 provides a reliable inspection of medicine preparation.

First person-authentication unit 32 has a biometric authentication function to identify inspectors 11 and 12 from their biological information, thereby preventing identity theft.

As shown in FIG. 1, medicine inspection support system 10 includes transfer container control device 14 and medicine shelf 16.

Medicine transfer container control device 14 includes inspector check unit 21. Medicine shelf 16 includes first person-authentication unit 32, first preliminary inspection unit 35, and first inspection unit 36.

Transfer container control device 14 is connected via the network to automated dispensing device 15 so as to provide device 15 with patient prescription information. Device 15 automatically puts medicines into transfer container 13 according to the patient prescription information stored in transfer container control device 14. Transfer container 13 can be a tray, an envelope, or the like into which medicines arranged for each patient are put.

Transfer container 13 containing the medicines dispensed from automated dispensing device 15 is transferred to medicine shelf 16 where the other medicines contained in the prescription information are put into transfer container 13.

Medicine shelf 16 contains medicines under supervised conditions such as narcotic and dangerous medicines to be managed by pharmacists, and other medicines that are seldom prescribed or too large to be stored in automated dispensing devices. These medicines stored in medicine shelf 16 are collectively referred to as specialty medicines.

Medicines dispensed from automated dispensing device 15, on the other hand, are prescribed very frequently and small enough in size to be stored therein. These medicines stored in device 15 are collectively referred to as general medicines.

The following is a detailed description of transfer container 13, transfer container control device 14, automated dispensing device 15, and medicine shelf 16. Transfer container 13 includes an identification tag such as an RFID or a bar code. This tag is used to detect the transfer container ID number, which is the unique ID number of transfer container 13. In the present first embodiment, the identification tag is bar-code tag 17.

Transfer container control device 14 includes transfer container information recording unit 20, inspector check unit 21, personnel information management unit 22, and LAN connection unit 23. Transfer container information recording unit 20 records the prescription information of each patient and his/her transfer container ID number. Inspector check unit 21 determines whether first preliminary inspector 11 and first inspector 12 are different persons. Personnel information management unit 22 records the personnel information about the medicine arranger and the inspector recorded in system 10. LAN connection unit 23 transmits and receives information to/from automated dispensing device 15 and medicine shelf 16 via LAN.

Automated dispensing device 15 includes ID number detection unit 27, dispensed medicine detection unit 26, and LAN connection unit 28. ID number detection unit 27 detects the transfer container ID number of transfer container 13 from bar-code tag 17. Dispensed medicine detection unit 26 detects medicine collection information about the medicines dispensed into transfer container 13. LAN connection unit 28 performs transmission and reception of information.

Medicine shelf 16 includes first display unit 31, first person-authentication unit 32, first ID-number detection unit 33, first preliminary inspection unit 35, first inspection unit 36, and LAN connection unit 37. First display unit 31 displays the names of the person-authentication unit 32 identifies first inspector 12 who performs an inspection of all medicines arranged in transfer container 13 at medicine shelf 16. Unit 32 also identifies first preliminary inspector 11 who performs a preliminary inspection of first medicines arranged in transfer container 13. First inspection unit 36 certifies that first inspector 12 has performed a first inspection of the general and first medicines arranged in transfer container 13.

First ID-number detection unit 33 detects the transfer container ID number of transfer container 13 from bar-code tag 17. Medicine shelf 16 further includes medicine collection information detection unit 34, which reads a medicine number from a bar code or other identifier on each first medicine when the medicine is taken out of medicine shelf 16 into transfer container 13. First preliminary inspection unit 35 certifies that first preliminary inspector 11 has performed a first preliminary inspection. LAN connection unit 37 performs transmission and reception of information. Medicine shelf 16 further includes medicine storage compartments 25, bar-code reader 24, and workbench 18.

The term "first medicine" in the present first embodiment indicates a specialty medicine stored in medicine shelf 16 of all the medicines shown on a prescription. When first inspector 12 performs an inspection, the names of all medicines on a prescription are displayed on first display unit 31, but the names of first medicines are highlighted in bold font, different colors, or by other means.

First person-authentication unit 32 has a biometric authentication function to perform person authentication using a fingerprint, facial features, a vein pattern, an iris pattern, or the like.

In system 10, inspector check unit 21 determines whether first inspector 12 is a different person from first preliminary inspector 11. When the determination is affirmative, inspectors 11 and 12 perform an inspection individually. Thus, medicine arrangement in transfer container 13 is inspected by more than one inspector, thereby providing a reliable inspection.

FIG. 3 is a flowchart of a medicine inspection support process. A medicine inspection procedure according to medicine inspection support system 10 of the present embodiment will be described as follows with reference to FIG. 3. First of all, upon receiving prescription information, automated dispensing device 15 dispenses medicines into transfer container 13 according to the prescription information (Step S01). The prescription information is transmitted to transfer container control device 14 through LAN connection unit 28 via the network, together with the transfer container ID number detected by ID number detection unit 27, and the medicine collection information obtained by dispensed medicine detection unit 26. All the information is recorded in transfer container information recording unit 20.

FIG. 4 shows a transfer container management table when the medicines are dispensed from automated dispensing device 15. Transfer container information recording unit 20 contains transfer container management table 29 shown in FIG. 4 to which the transfer container ID number, the prescription information, and the dispensing-device-medicine-collection-information have been newly added.

The newly added information: the transfer container ID number, the prescription information, and the dispensing-device-medicine-collection-information are shown in the row of the transfer container ID: "0004" in table 29 of FIG. 4.

Transfer container 13 containing the medicines dispensed from automated dispensing device 15 is transferred to medicine shelf 16. Then, first preliminary inspector 11, who is the first medicine-arranger, takes necessary medicines out of medicine storage compartments 25 in medicine shelf 16, and arranges them in transfer container 13 (Step S02). First preliminary inspector 11 performs a first preliminary inspection of the arrangement of the first medicines at medicine shelf 16 (Step S03).

First preliminary inspector 11 informs first inspector 12 of the completion of the first preliminary inspection. Next, first inspector 12 performs a first inspection of all medicines arranged in transfer container 13 (Step S04). All medicines here indicate the general medicines from the automated dispensing device and the first medicines from the medicine shelf.

Thus, according to medicine inspection support system 10, medicine preparation and the inspection of the medicine preparation are performed at medicine shelf 16 by first preliminary inspector 11 and first inspector 12, who should be different persons.

The following is a detailed description of the medicine arrangement at Step S02 and the first preliminary inspection at Step S03.

Figure 5:
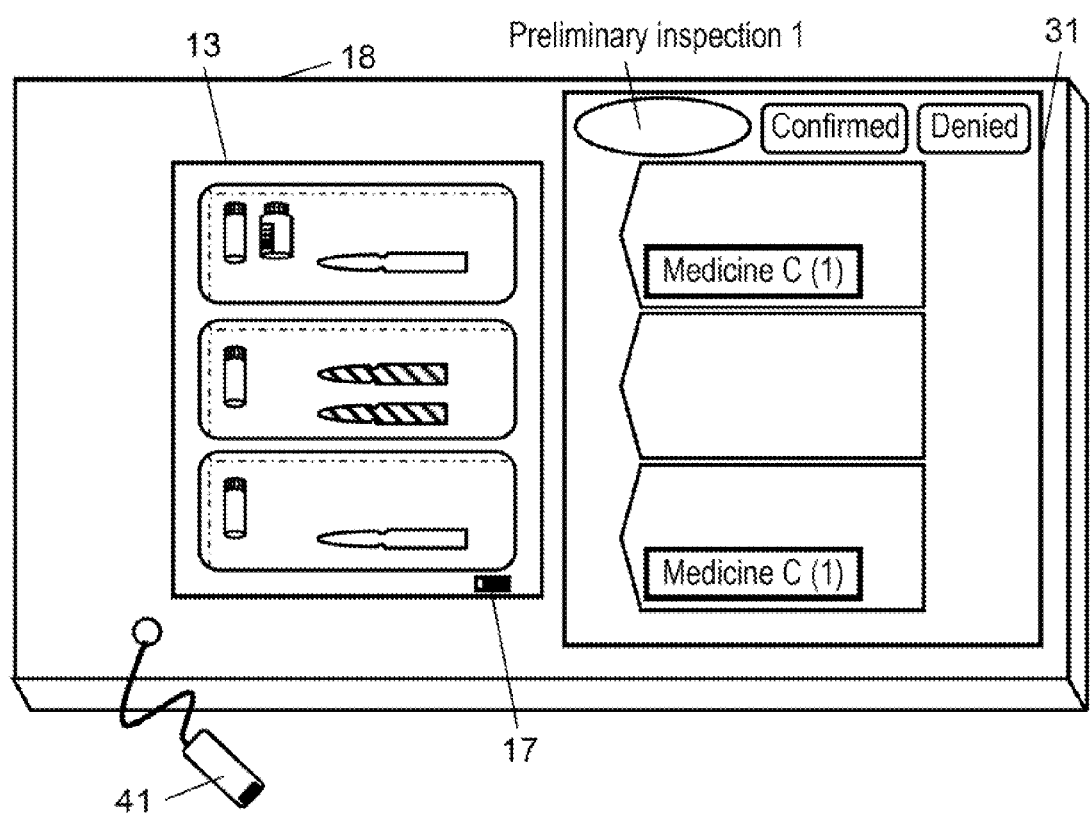
FIG. 5 is an overhead view of a workbench of a medicine shelf on which medicines are arranged according to the first embodiment of the invention.

FIG. 5 is an overhead view of workbench 18 of medicine shelf 16 while medicines are being arranged. As shown in FIG. 5, workbench 18 includes first display unit 31, which is a touch monitor. The first medicine-arranger puts transfer container 13 on the space provided therefor adjacent to first display unit 31.

Figure 6:
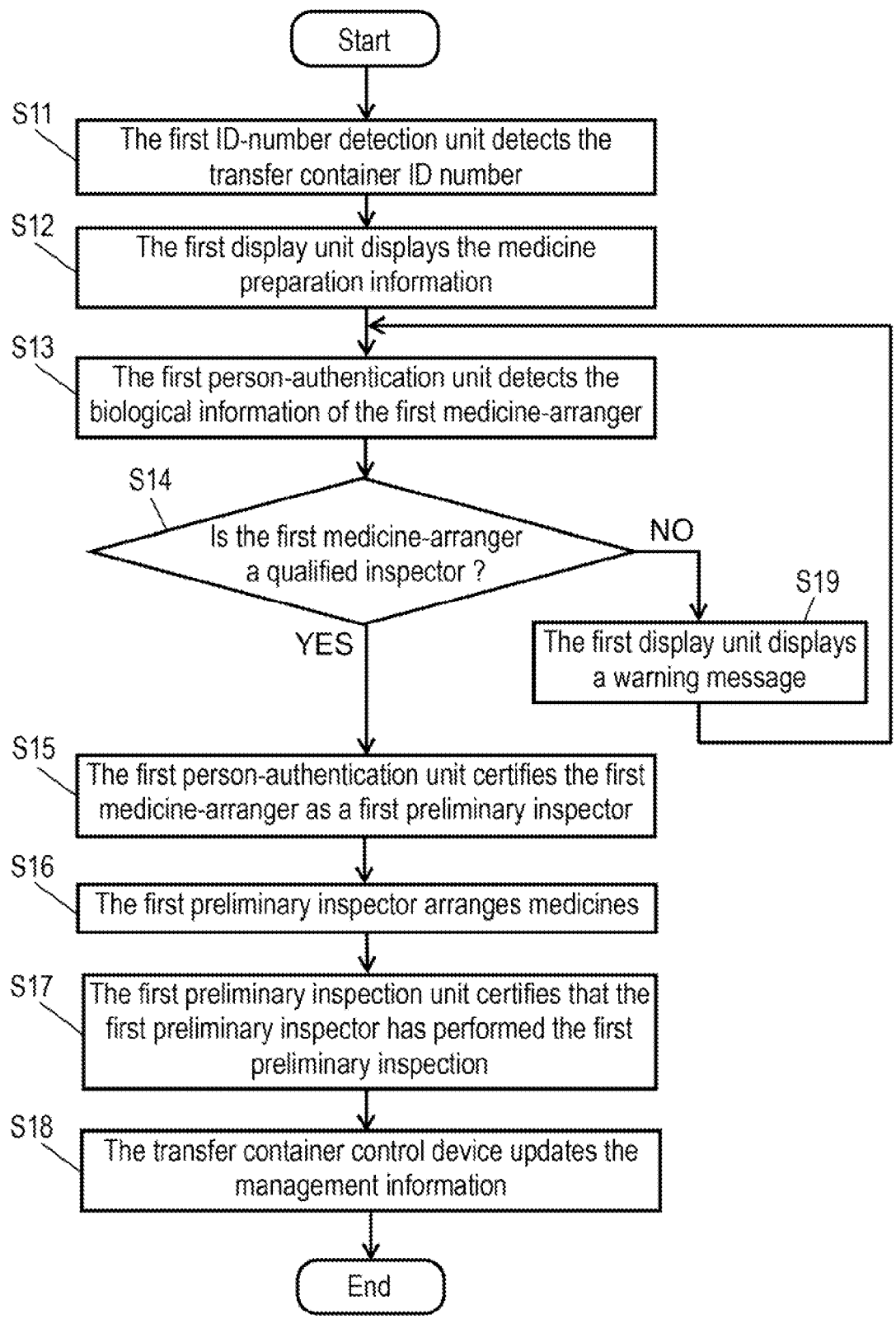
FIG. 6 is a flowchart of medicine arrangement and a first preliminary inspection according to the first embodiment of the invention.

FIG. 6 is a flowchart of the medicine arrangement and the first preliminary inspection at medicine shelf 16. As shown in FIG. 6, bar-code tag 17 of the placed transfer container 13 is scanned with bar-code reader 41 so that first ID-number detection unit 33 detects the transfer container ID number (Step S11). Bar-code reader 41 is the mouth of first ID-number detection unit 33. The detection of the transfer container ID number is performed by unit 33. Bar-code tag 17 may be replaced by a RFID, which can detect a transfer container ID number without the use of hands.

The transfer container ID number thus scanned is transferred through LAN connection unit 37 to transfer container information recording unit 20 of transfer container control device 14. The ID number is compared against a list of transfer container management table 29 so as to pick out the prescription information indicating the medicines to be arranged in transfer container 13. The prescription information thus picked out is transferred from device 14 to medicine shelf 16. Medicine shelf 16 forms medicine preparation information which indicates the first medicines to be arranged at medicine shelf 16 according to the prescription information. Then, first display unit 31 displays the medicine preparation information (Step S12).

The first medicines displayed on first display unit 31 are medicines available from medicine shelf 16. While the first medicines are being arranged, first display unit 31 displays their names and numbers in correspondence with the respective areas of transfer container 13. More specifically, the names and numbers of these medicines are displayed in the three areas of transfer container 13 shown in FIG. 5. The three areas are provided for medicines to be taken in the morning, noon, and evening, respectively.

Then, the first medicine-arranger uses first person-authentication unit 32 so as to be certified as first preliminary inspector 11 as follows. First of all, first person-authentication unit 32 detects the biological information of the first medicine-arranger (Step S13). Unit 32 then makes an inquiry to personnel information management unit 22 of transfer container control device 14 about who is the first medicine-arranger identified by iris recognition, and whether he/she has a pharmacist license. In other words, unit 32 determines whether the first medicine-arranger is a qualified inspector (Step S14).

When it has been determined that the first medicine-arranger is registered in personnel information management unit 22 and has a pharmacist license, he/she is permitted to perform medicine arrangement. Then, first person-authentication unit 32 certifies the first medicine-arranger as first preliminary inspector 11 (Step S15).

In this manner, first preliminary inspector 11 is identified through Steps S13, S14, and S15.

The first medicine-arranger takes a medicine C out of medicine storage compartment 25, scans the bar code on the bottle or other type of container of the medicine C with bar-code reader 24, and puts the medicine C into transfer container 13. Bar-code reader 24 is the mouth of medicine collection information detection unit 34, which detects the medicine collection information. Thus, first preliminary inspector 11, who is the first medicine-arranger, arranges medicines at first medicine shelf 16 (Step S16).

The bar code on the bottle or other type of container of the medicine C can be scanned with bar-code reader 41 instead of bar-code reader 24.

After completing the medicine arrangement in transfer container 13, the first medicine-arranger performs a first preliminary inspection as first preliminary inspector 11 to check whether the medicine arrangement has been done correctly. When first preliminary inspector 11 has determined that the medicine arrangement has been done correctly, first preliminary inspection unit 35 certifies that first preliminary inspector 11 has performed the first preliminary inspection (Step S17). The certification is achieved by first preliminary inspector 11 touching the letter "Confirmed" shown on first display unit 31 as shown in FIG. 5.

The following information is transferred from medicine shelf 16 to transfer container control device 14, and added to transfer container management table 29 stored in transfer container information recording unit 20. The information includes the information about the first preliminary inspector identified by first person-authentication unit 32, and the medicine collection information and the transfer container management number obtained by medicine collection information detection unit 34. Thus, transfer container control device 14 updates the management information held in transfer container information recording unit 20 (Step S18).

When the first medicine-arranger has been determined not to be a qualified inspector in Step S14, first display unit 31 displays a warning message (Step S19). Then, the process returns to Step S13.

After completing the first preliminary inspection, the first medicine-arranger informs first inspector 12 of the completion. Next, first inspector 12 performs an inspection of the medicine arrangement in transfer container 13.

The following is a detailed description of the first inspection in Step S04.

Figure 7:
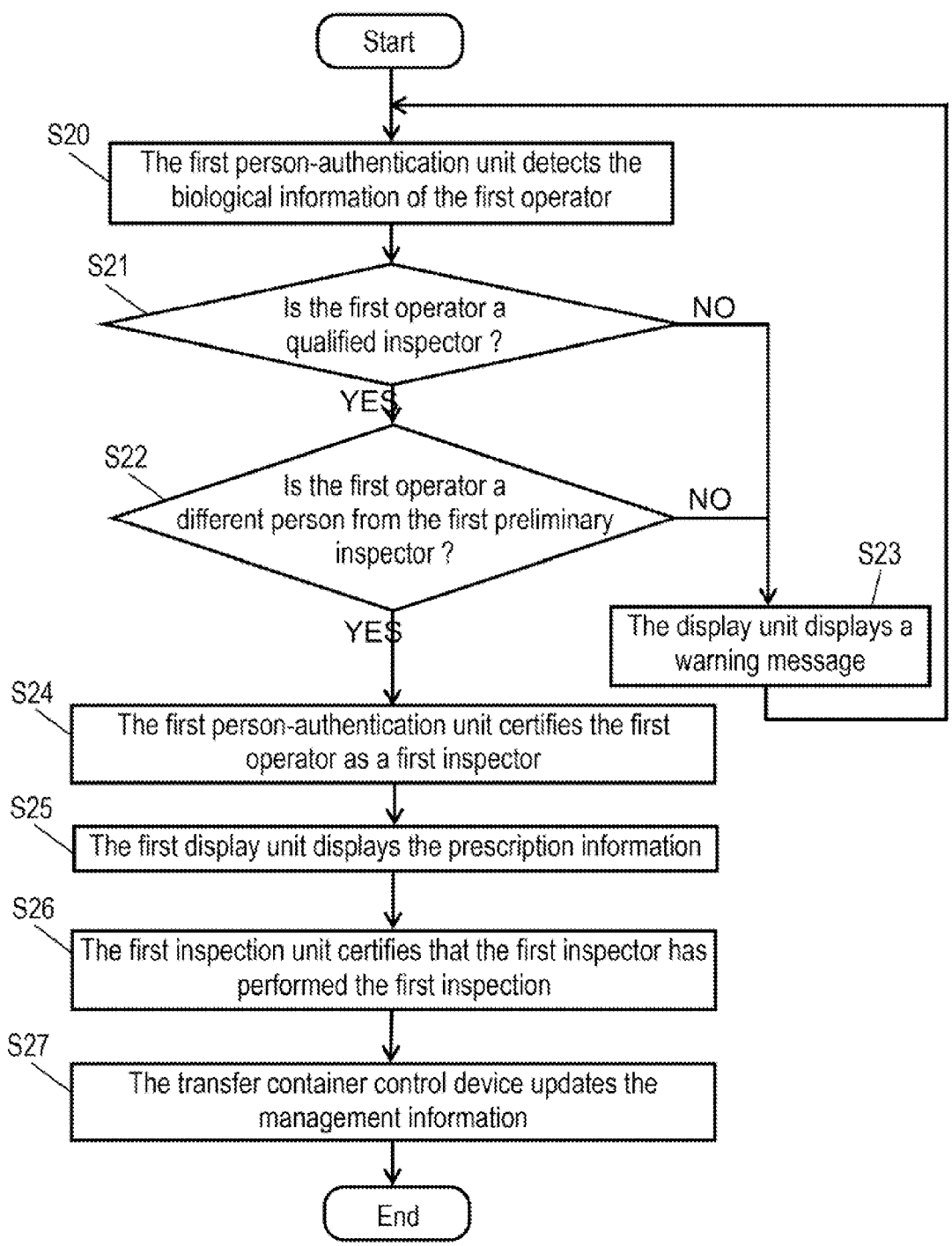
FIG. 7 is a flowchart of a first inspection according to the first embodiment of the invention.

FIG. 7 is a flowchart of the first inspection. As shown in FIG. 7, a first operator uses first person-authentication unit 32' so as to be certified as first inspector 12 as follows. First of all, first person-authentication unit 32 detects the biological information of the first operator (Step S20).

Unit 32 then makes an inquiry to personnel information management unit 22 about who is the first operator and whether he/she has a pharmacist license. In other words, unit 32 determines whether the first operator is a qualified inspector (Step S21).

Inspector check unit 21 determines whether the first operator is a different person from first preliminary inspector 11 (Step S22). Having been determined to have a pharmacist license and to be a different person from first preliminary inspector 11, the first operator is permitted to perform a first inspection. Then, first person-authentication unit 32 certifies the first operator as first inspector 12 (Step S24).

In this manner, first inspector 12 is identified through Steps S20, S21, S22, and S24.

On the other hand, when the first operator has been determined not to be a qualified inspector or to be the same person as the first preliminary inspector, first display unit 31 displays a warning message (Step S23). When, for example, the first operator has been determined to be the same person as the first preliminary inspector, first display unit 31 displays a warning message: "Sorry, please get another operator to perform the inspection". Then, the process returns to Step S20.

When first inspector 12 has been certified, first display unit 31 displays the prescription information of transfer container 13 (Step S25).

Figure 8:
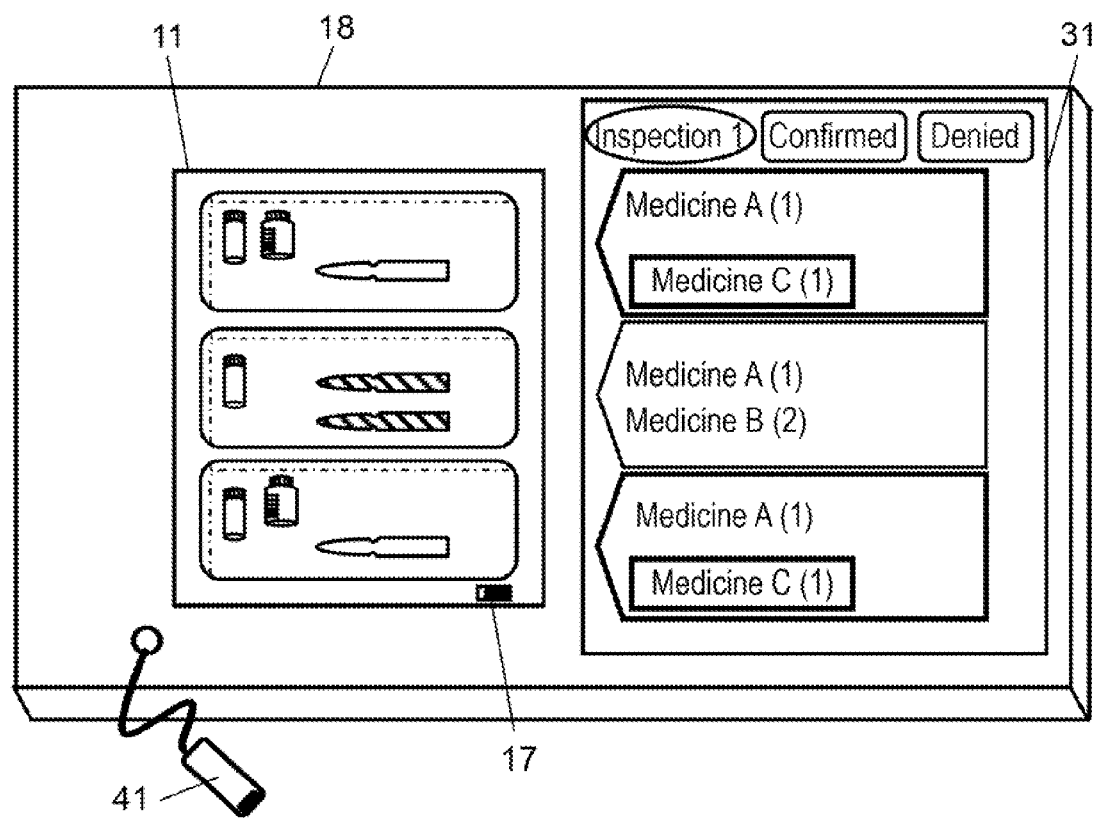
FIG. 8 is an overhead view of the workbench of the medicine shelf on which a first inspection is performed according to the first embodiment of the invention.

FIG. 8 is an overhead view of workbench 18 of medicine shelf 16 on which a first inspection is performed. The name and the number of the medicine (the medicine C) which is the first medicine to be arranged in transfer container 13 at medicine shelf 16 are displayed more prominently than those of the other medicines as shown in FIG. 8. First inspector 12 inspects as to whether the medicine arrangement in transfer container 13 has been done correctly by referring to the information displayed on first display unit 31. Having determined that the arrangement has been done correctly, first inspector 12 touches the letter "Confirmed" shown on first display unit 31. As a result, first inspection unit 36 certifies that first inspector 12 has performed the first inspection (Step S26).

The information about the first inspector identified by first person-authentication unit 32 is transferred to transfer container control device 14, and added to transfer container management table 29 stored in transfer container information recording unit 20. In other words, transfer container control device 14 updates the management information held in unit 20 (Step S27).

As described hereinbefore, medicine inspection support system 10 requires first preliminary inspector 11 and first inspector 12 at medicine shelf 16 to be different persons. This prevents first preliminary inspector 11 from impersonating first inspector 12 and performing a first inspection. As a result, medicine arrangement becomes more reliable.

In the flowchart of FIG. 6, displaying the medicine preparation information is performed in Step S12 before first preliminary inspector 11 is certified in Step S15, but may alternatively be performed after Step S15. In the latter case, the medicine preparation information is provided only when first inspector 12 has been identified, and therefore, is accessible only to inspectors 11 and 12, thereby improving the security.

First preliminary inspector 11 and first inspector 12 are registered as licensed pharmacists in personnel information management unit 22 and actually have the same qualification. Therefore, the preliminary inspection by first preliminary inspector 11 and the inspection by the first inspector are actually performed in the same manner by two different inspectors.

The qualifications of the preliminary inspector and the inspector may be changed according to the circumstances, or the preliminary inspector may be certified based on fewer requirements than in the case of the inspector. For example, a pharmacy technician, who is not a licensed pharmacist, can be registered as a preliminary inspector in a personnel information management unit 22.

In the above-described medicine inspection support system 10, inspector check unit 21 is included in transfer container control device 14, but may alternatively be included in medicine shelf 16.

In the above-described medicine inspection support system 10, medicines are taken out of medicine storage compartments 25 in medicine shelf 16, but may alternatively be brought in from another place. For example, in the case of medicine-solution mixing, injection solutions can be brought in from an injection solution cabinet (not shown) away from workbench 18, and be mixed on workbench 18.

An inspection of medicine preparation is performed to check whether the medicine preparation has been done properly according to a prescription. It also checks whether the types and the numbers of medicines are in accordance with the prescription; whether the medicines are properly combined with each other; whether the lifetime dosage is appropriate for the patient; and whether the medicines are safe for a pregnant or allergic patient.

Second Embodiment

Medicine inspection support system 10 of a second embodiment of the invention differs from system 10 of the first embodiment in that first inspector 12 is identified after first preliminary inspector 11 is identified and before a first preliminary inspection is performed.

In the first embodiment, first inspector 12 is identified by first person-authentication unit 32 after a first inspection. In the second embodiment, on the other hand, when first preliminary inspector 11 as a mixing operator is mixing medicines, first inspector 12 performs a first inspection by watching the mixing.

Therefore, first person-authentication unit 32 needs to certify first inspector 12 before the first preliminary inspection is completed. Medicine inspection support system 10 requires a double inspection by two persons in various types of medicine preparation, thereby providing a highly reliable inspection of medicine preparation.

Medicine inspection support system 10 of the present second embodiment is structured the same, but controlled differently from system 10 of the first embodiment as follows.

The medicine preparation includes medicine mixing in addition to medicine arrangement for arranging a required number of necessary medicines. The medicine mixing includes medicine-solution mixing in which a medicine solution is sucked from a vial into a syringe, and a required amount of the medicine solution is injected into an infusion bag.

The medicine-solution mixing is inspected by the mixing operator. When the mixing operator performs the medicine mixing, the inspector watches it while standing besides the workbench. For example, when injecting 50 ml of a medicine solution F into an infusion bag, the mixing operator says to the inspector "I'm going to inject 50 ml of a medicine solution F into the infusion bag". The inspector watches to make sure that the mixing operator injects 50 ml of the medicine solution F into the infusion bag. Thus, a double inspection of the medicine-solution mixing is performed by first preliminary inspector 11 who is the mixing operator, and first inspector 12.

Figure 9:
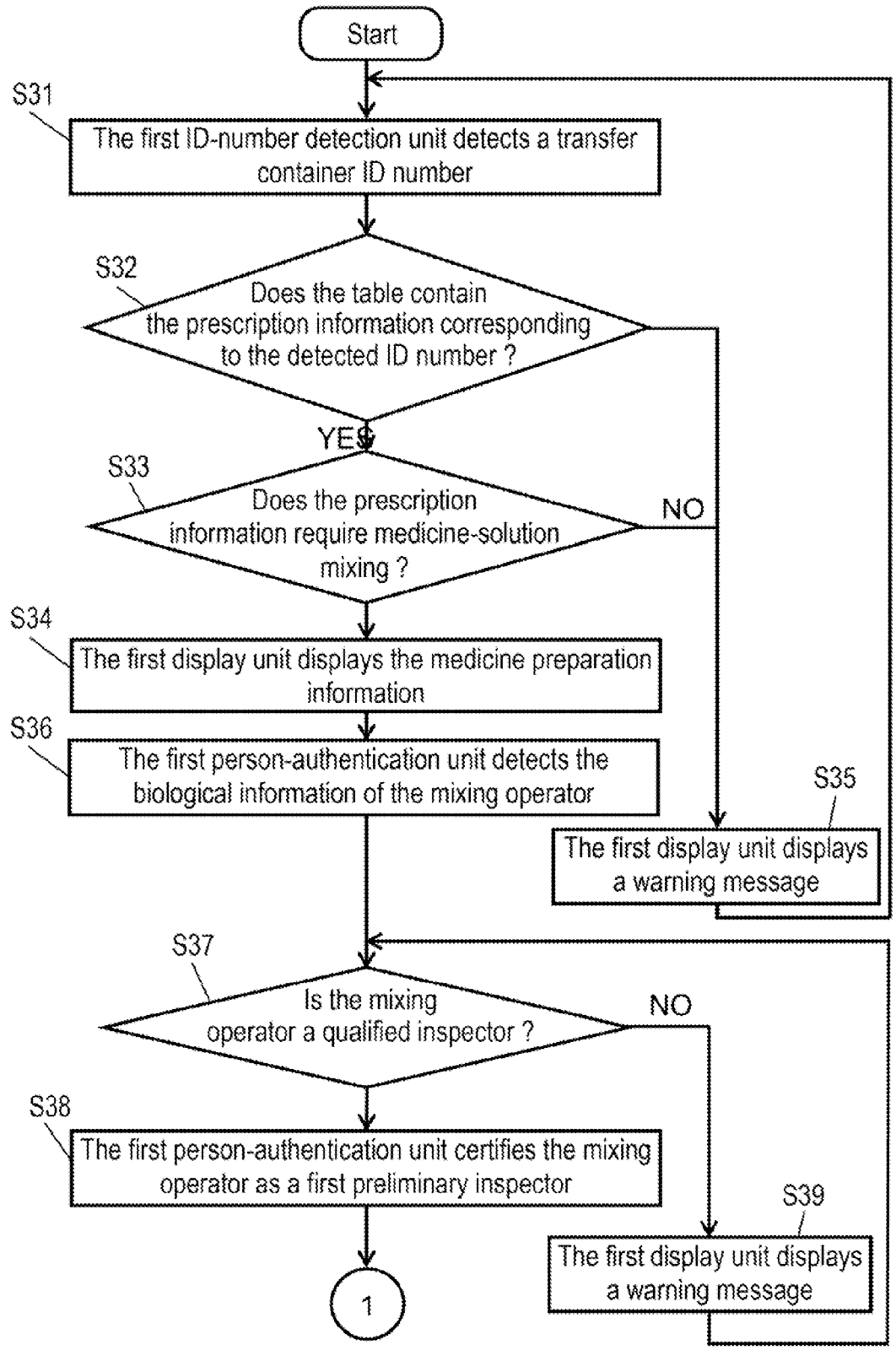
FIG. 9 is a first flowchart of a first preliminary inspection and a first inspection according to a second embodiment of the invention.
Figure 10:
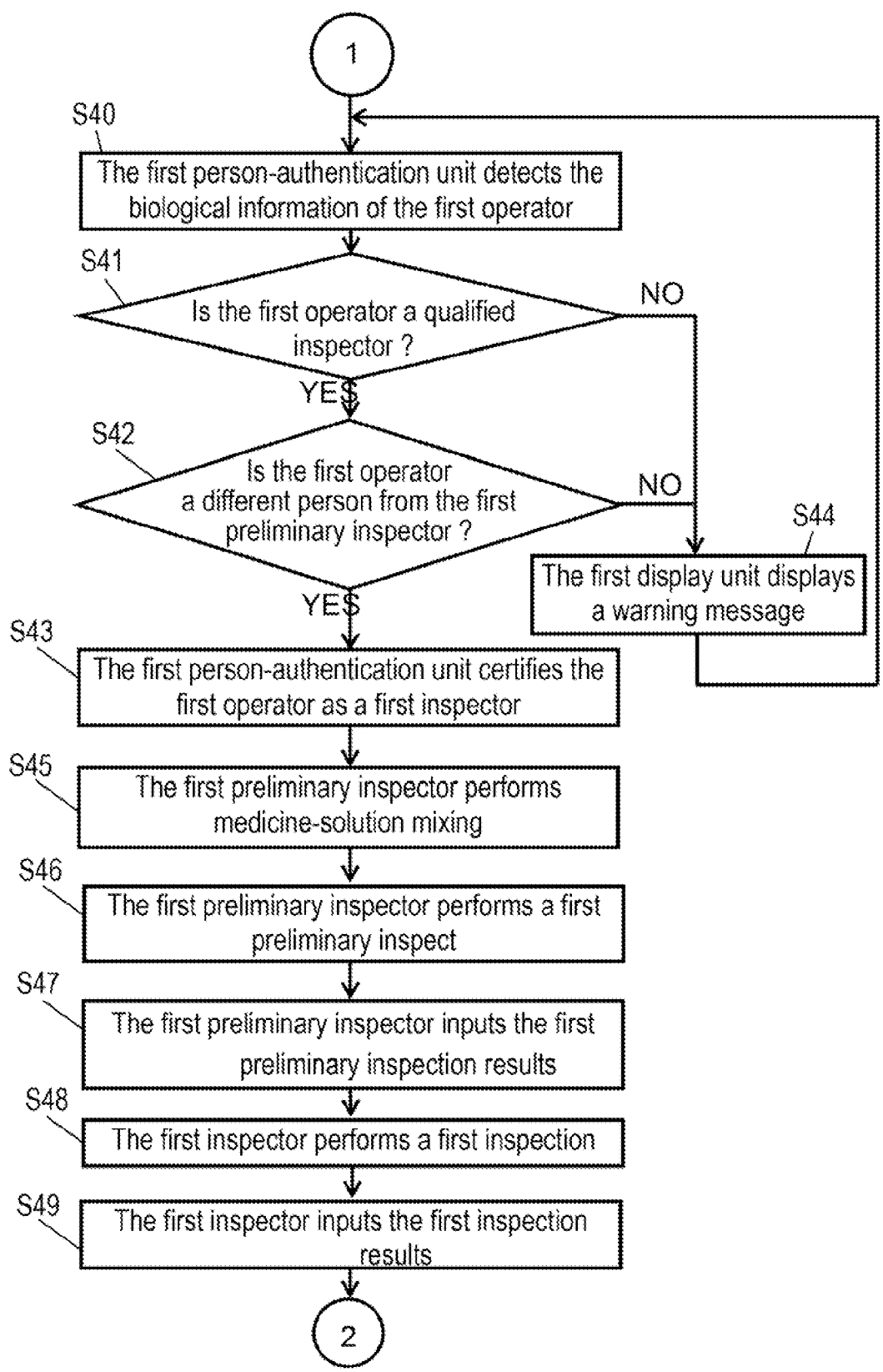
FIG. 10 is a second flowchart of the first preliminary inspection and the first inspection according to the second embodiment of the invention.
Figure 11:
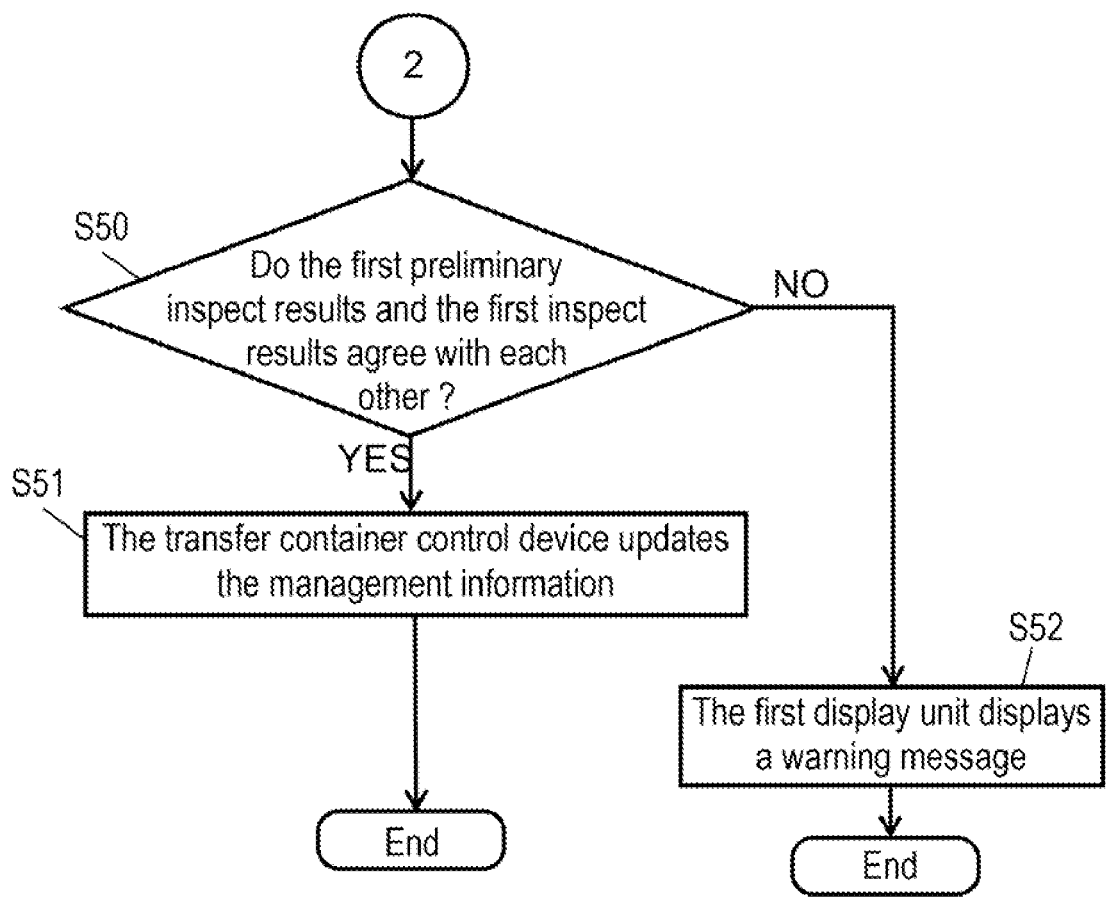
FIG. 11 is a third flowchart of the first preliminary inspection and the first inspection according to the second embodiment of the invention.

Medicine inspection support system 10 of the present, second embodiment has the same structure as system 10 of the second embodiment. FIGS. 9, 10, and 11 are a flowchart of the medicine-solution mixing based on system 10.

First of all, the mixing operator switches the medicine preparation mode of medicine shelf 16 from an arrangement mode to a medicine mixing mode. Then, the mixing operator prepares syringes and other tools necessary for the medicine-solution mixing, and scans bar-code tag 17 of transfer container 13 containing medicines to be mixed with bar-code reader 41. As a result, as shown in FIG. 9, first ID-number detection unit 23 detects a transfer container ID number (Step S31).

Then, first ID-number detection unit 23 transmits the transfer container ID number to transfer container control device 14. Device 14 compares this ID number against a list of transfer container management table 29 so as to determine whether table 29 contains the prescription information corresponding to the ID number (Step S32). When table 29 has been determined to contain the prescription information, device 14 determines whether the prescription information requires medicine-solution mixing (Step S33). When the determination is affirmative, the prescription information is transferred to medicine shelf 16.

Upon receiving the prescription information, medicine shelf 16 extracts medicine preparation information required for the medicine-solution mixing, and first display unit 31 displays the medicine preparation information (Step S34).

When there is no prescription information in Step S32 or when the prescription information does not require medicine solution mixing in Step S33, first display unit 31 displays a warning message (Step S35) indicating that transfer container 13 does not require medicine solution mixing.

The mixing operator uses first person-authentication unit 32 so as to be certified as first preliminary inspector 11 as follows.

First of all, first person-authentication unit 32 detects the biological information of the mixing operator (Step 36). Then, transfer container control device 14 determines whether the mixing operator is a qualified inspector (Step S37). The mixing operator is determined to be a qualified inspector if he/she is registered in personnel information management unit 22 and has a pharmacist license.

When the mixing operator is a qualified inspector, first person-authentication unit 32 of medicine shelf 16 certifies the mixing operator as first preliminary inspector 11 (Step S38).

In this manner, the first preliminary inspector 11 is identified through Steps S36, S37, and S38.

As a result, the mixing operator can perform medicine-solution mixing and the preliminary inspection of the medicine-solution mixing at medicine shelf 16.

When the mixing operator has been determined not to be a qualified inspector in Step S37, on the other hand, first display unit 31 displays a warning (Step S39) indicating that this operator is not a qualified inspector. When the first preliminary inspector has been certified in Step S38, a first operator uses first person-authentication unit 32 so as to be certified as first inspector 12 as follows.

As shown in FIG. 10, first person-authentication unit 32 detects the biological information of the first operator, who becomes first inspector 12 (Step S40).

Unit 32 then determines whether the first operator is a qualified inspector (Step S41). The first operator is determined to be a qualified inspector if he/she is registered in personnel information management unit 22 and has a pharmacist license.

When the first operator is a qualified inspector, inspector check unit 21 determines whether the first operator is a different person from first preliminary inspector 11 (Step S42).

When the determination is affirmative, first person-authentication unit 32 certifies the first operator as a first inspector (Step S43).

In this manner, first inspector 12 is identified through Steps S40, S41, S42, and S43.

When the first operator has been determined not to be a qualified inspector in Step S41, first display unit 31 displays a warning message. Similarly, when the first operator 12 has been determined to be the same person as first preliminary inspector 11, first display unit 31 displays a warning message (Step S44).

When first inspector 12 is certified in Step S43, first preliminary inspector 11, who is the mixing operator, performs medicine-solution mixing (Step S45). First inspector 12 watches the medicine-solution mixing of first preliminary inspector 11. When the medicine-solution mixing indicated in the medicine preparation information displayed on first display unit 31 has been all completed, first preliminary inspector 11 confirms the medicine preparation information and performs an inspection of the medicine-solution mixing. In other words, the mixing operator performs a first preliminary inspection of the medicine-solution mixing as first preliminary inspector 11 (Step S46). Then, first preliminary inspector 11 inputs the first preliminary inspection results of the medicine-solution mixing to medicine shelf 16 (Step S47). In other words, first preliminary inspector 11 confirms or denies the first preliminary inspection.

Next, first inspector 12 performs a first inspection of the medicine-solution mixing done by first preliminary inspector 11 (Step S48). The first inspector confirms the medicine preparation information so as to make sure that the medicine-solution mixing has been properly performed. Then, first inspector 12 inputs the first inspection results of the medicine-solution mixing to medicine shelf 16 (Step S49). In other words, first inspector 12 confirms or denies the first inspection. Then, it is determined whether the first preliminary inspection results and the first inspection results agree with each other (Step S50) as shown in FIG. 11.

When the determination is affirmative, the information about inspectors 11 and 12, and the inspection results are added to transfer container management table 29 stored in transfer container information recording unit 20. In other words, transfer container control device 14 updates the management information (Step S51).

When the determination is negative in Step S51, on the other hand, first display unit 31 displays a warning message (Step S52) indicating disagreement between the first preliminary inspection results and the first inspection results.

Medicine inspection support system 10 requires a double inspection by two inspectors in various types of medicine preparation, thereby providing a highly reliable inspection of medicine preparation. The medicine-solution mixing may include checking dust and dirt on infusion bags after the mixing, and also include inspecting an automated mixer.

The medicine preparation includes dividing and packaging of medicines in which powdered medicine is packaged into individual doses. The inspector watches the medicine preparation operator perform the dividing and packaging of medicines while standing besides him/her. Thus, a double inspection is performed by the medicine preparation operator and the inspector.

The medicine preparation further includes administration of medicines to hospital inpatients. The administration of medicines includes confirming the presence or absence, the amounts, and the types of medicines to be given by mouth, through a drip, and by an injection to patients.

Two nurses carry a medication cart and give medicines to patients. Medicine inspection support system 10 can be applied to medication carts so as to achieve reliable administration of medicines.

Third Embodiment

According to the medicine inspection support system of a third embodiment of the invention, in the case where the first inspector is the same person as the first preliminary inspector, he/she is permitted to perform a first inspection, provided that the time elapsed since a first operation certification time has reached or exceeded a refresh time.

The "refresh time" means the time required for an inspector to refresh and recover from the fatigue of an inspection that requires intense concentration. In the present third embodiment, the refresh time is set to one hour which is generally considered to allow people to refresh and recover.

Figure 12:
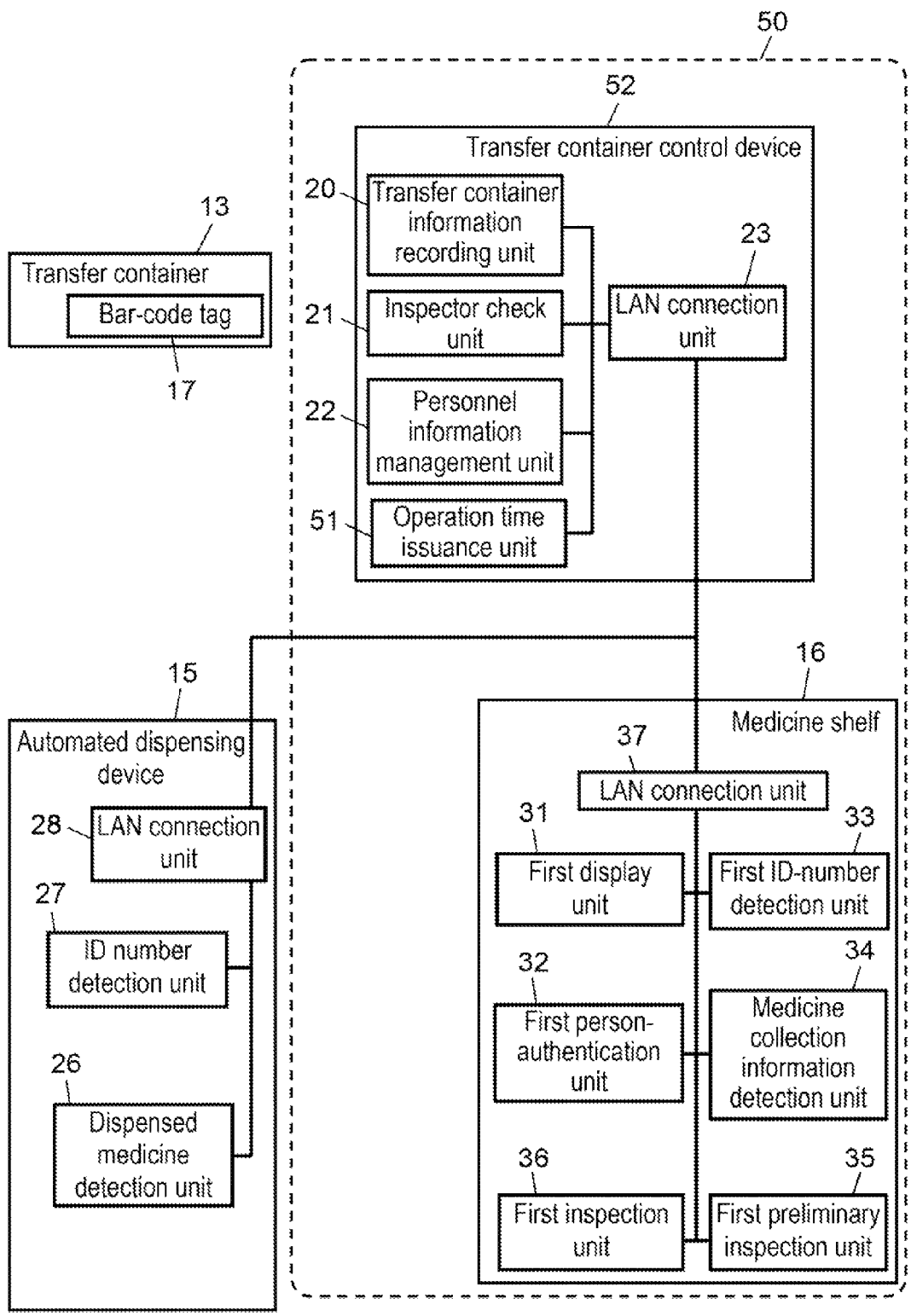
FIG. 12 is a block diagram of a medicine inspection support system according to a third embodiment of the invention.

FIG. 12 is a block diagram of medicine inspection support system 50' according to the third embodiment. As shown in FIG. 12, system 50 includes operation time issuance unit 51, which issues a first operation certification time and a second operation certification time. The first operation certification time is when first preliminary inspection unit 35 certifies a preliminary inspection of medicine preparation. The second operation certification time is when first inspector 12 is identified.

Having determined that first inspector 12 is the same person as first preliminary inspector 11, inspector check unit 21 permits first inspection unit 36 to certify completion of the inspection when the time difference between the first and second operation certification times is not less than the refresh time.

Therefore, the first preliminary inspector who has performed a first preliminary inspection can perform a first inspection when the refresh time has passed since the first preliminary inspection.

Thus, the same person can perform both a first preliminary inspection and a first inspection with the refresh time therebetween, thereby providing a reliable inspection.

Medicine inspection support system 50 of the present third embodiment is obtained by adding operation time issuance unit 51 to medicine inspection support system 10.

In the case where first inspector 12 is the same person as first preliminary inspector 11, inspector check unit 21 permits an inspection to be performed upon the satisfaction of the condition that the interval between the first and second operation times is not less than the refresh time. The first operation time is when first preliminary inspection unit 35 certifies a preliminary inspection, and the second operation time is when first person-authentication unit 32 identifies the first inspector.

If the same inspector performs a first preliminary inspection and a first inspection in quick succession, he/she tends to be affected by the results of the first preliminary inspection while performing the first inspection.

It is, however, considered that an interval of one hour or more between these inspects can refresh the inspector's thought process, allowing him/her to perform the first inspection without the influence of the first preliminary inspection.

Medicine inspection support system 50 includes transfer container control device 52, which includes transfer container information recording unit 20, inspector check unit 21, personnel information management unit 22, LAN connection unit 23, and operation time issuance unit 51, which issues the above-described operation times.

Transfer container information recording unit 20 records the prescription information of each patient, transfer container ID numbers and other information. Inspector check unit 21 determines whether first inspector 12 is a different person from first preliminary inspector 11. Personnel information management unit 22 records the personnel information about the medicine arranger and the inspector recorded in medicine inspection support system 50. LAN connection unit 23 transmits and receives information to/from automated dispensing device 15 and medicine shelf 16 via LAN. Operating time issuance unit 51 issues operation certification times to transfer container control device 52.

Medicine inspection support system 50 operates as follows. First of all, transfer container 13 is put on workbench 18 of medicine shelf 16. The medicines in transfer container 13 are subjected to a first preliminary inspection. When first preliminary inspector 11 determines that the medicine arrangement has been done correctly, first preliminary inspection unit 35 certifies the first preliminary inspection. Then, the information about the first inspector is added to the transfer container management table. At the same time, operation time issuance unit 51 issues the first operation certification time, which is also added to the management table.

Next, a first inspection is performed at medicine shelf 16 as follows. The information about the first preliminary inspector contained in the same transfer container on the transfer container management table is extracted according to the transfer container ID number scanned with bar-code reader 41. Then, inspector check unit 21 compares the information about the first preliminary inspector contained in the management table with the information about the first inspector obtained from first person-authentication unit 32 so as to determine whether first preliminary inspector 11 and first inspector 12 are different persons.

In the case where these inspectors 11 and 12 are the same person, the first operation certification time is extracted from the transfer container management table. Furthermore, inspector check unit 21 asks operation time issuance unit 51 to issue the current operation time, which is made the second operation certification time.

Inspector check unit 21 calculates whether the interval between the first and second operation certification times has passed the refresh time of one hour or more. When the interval has passed the refresh time, first inspector 12, who is also first preliminary inspector 11, is permitted to perform a first inspection. First display unit 31 displays the names and numbers of the medicines contained in the prescription information so that the first inspection can be performed.

If the interval has not passed the refresh time, on the other hand, first preliminary inspector 11 is not permitted to perform a first inspection. Thus, a reliable inspection can be performed by a single inspector.

Fourth Embodiment

The medicine inspection support system according to a fourth embodiment of the invention includes a first medicine-preparation unit, a second medicine-preparation unit, and an inspector check unit. The first medicine-preparation unit is where a first inspector performs a first inspection, and the second medicine-preparation unit is where a second inspector performs a second inspection. The inspector check unit permits the second inspection unit of the second medicine-preparation unit to certify completion of the inspection when the second inspector has been determined to be a different person from the first inspector.

A series of medicine preparations performed in different locations is inspected by different first and second inspectors, thereby achieving reliable medicine preparation.

Figure 13:
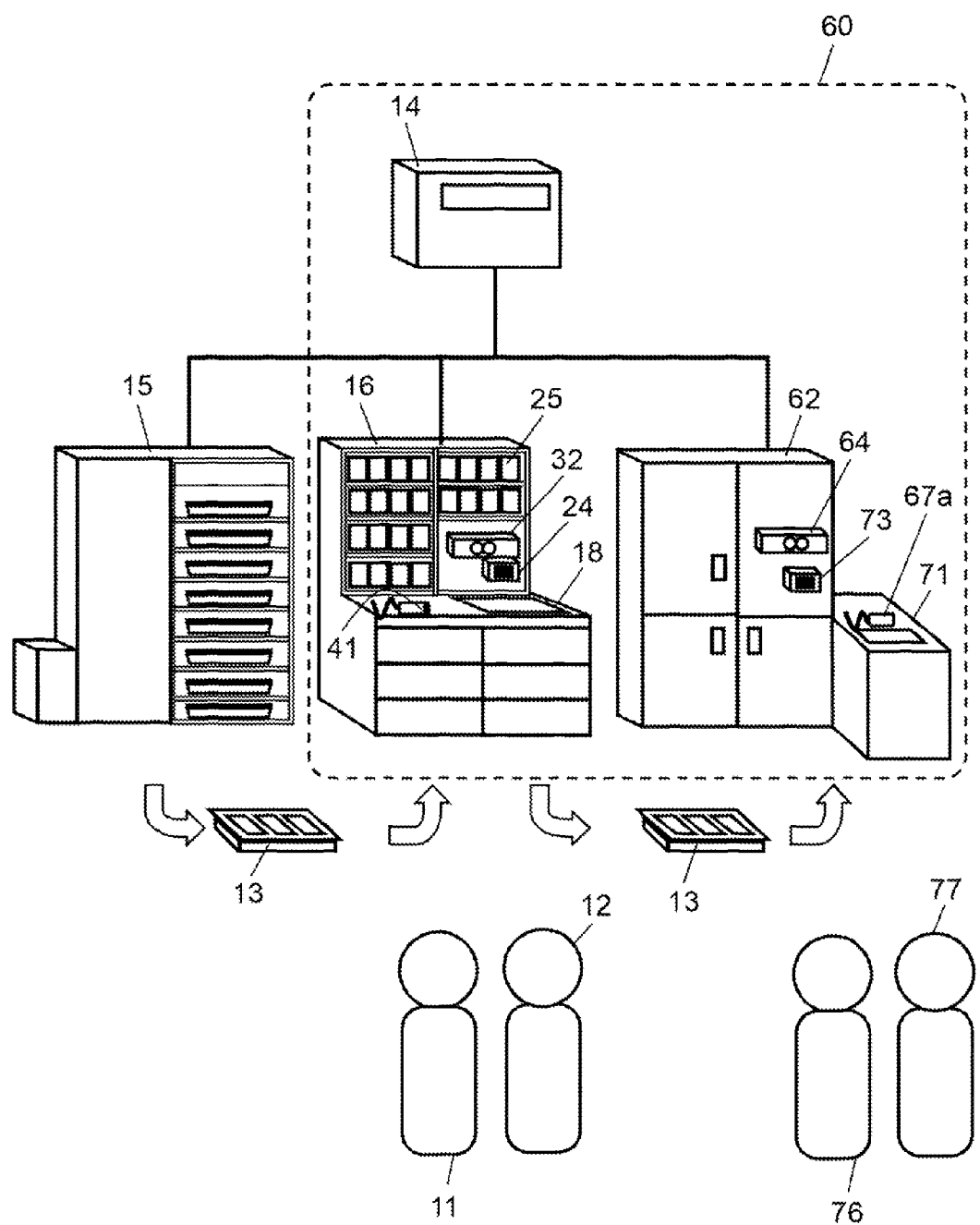
FIG. 13 is a schematic configuration view of a medicine inspection support system according to a fourth embodiment of the invention.
Figure 14:
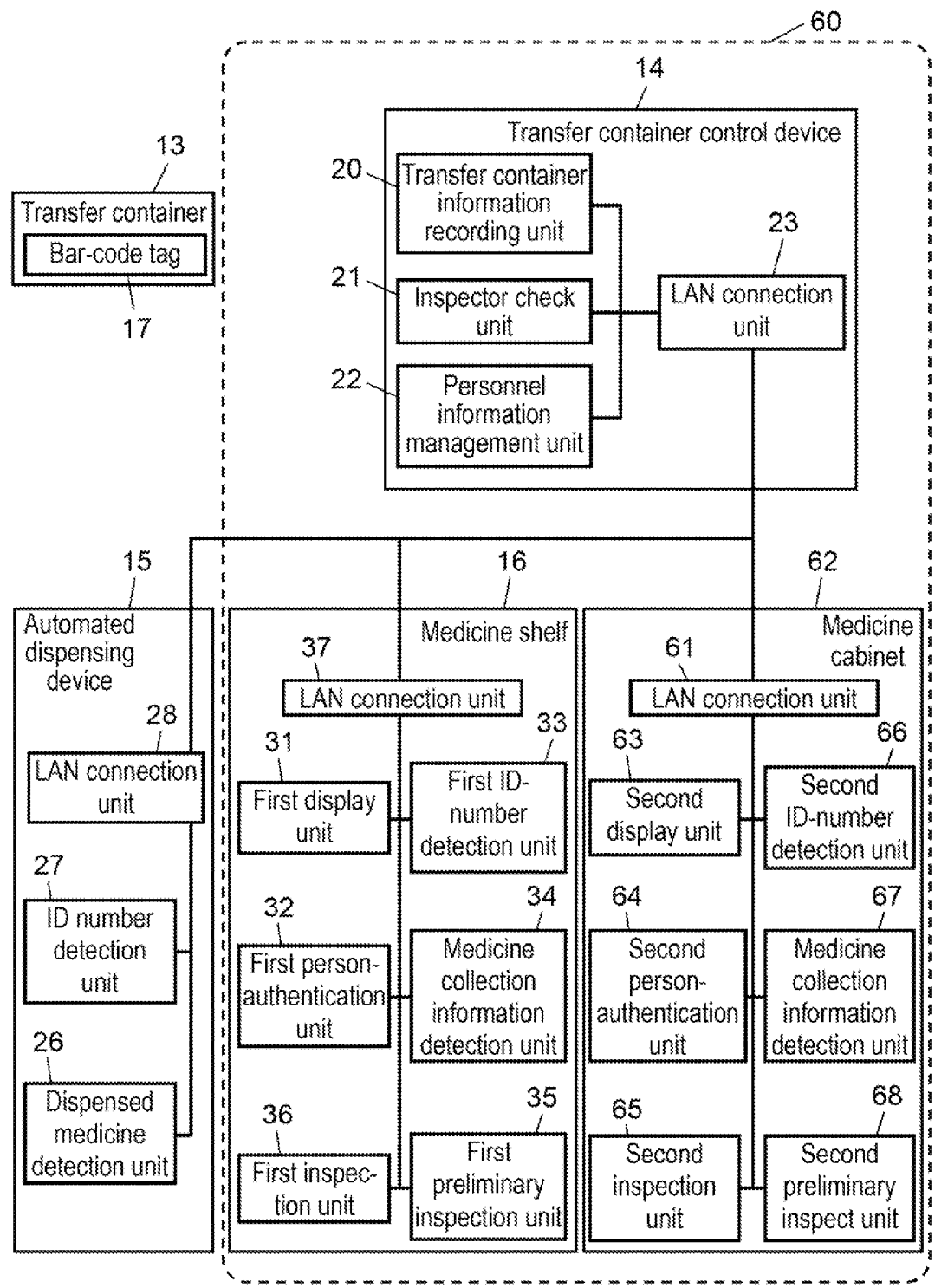
FIG. 14 is a block diagram of the medicine inspection support system according to the fourth embodiment of the invention.

FIG. 13 is a schematic configuration view of medicine inspection support system 60 according to the fourth embodiment. FIG. 14 is a block diagram of system 60.

As shown in FIGS. 13 and 14, medicine inspection support system 60 includes medicine shelf 16 provided for first medicine-preparation, medicine cabinet 62 provided for second medicine-preparation, and transfer container control device 14. Medicine shelf 16 is the first medicine-preparation unit, and medicine cabinet 62 is the second medicine-preparation unit.

Medicine shelf 16 includes first person-authentication unit 32 and first inspection unit 36. First person-authentication unit 32 identifies first inspector 12 who performs an inspection at medicine shelf 16. First inspection unit 36 certifies that first inspector 12 has performed a first inspection at medicine shelf 16.

Medicine cabinet 62 includes second person-authentication unit 64 and second inspection unit 65. Second person-authentication unit 64 identifies second inspector 77, who performs an inspection at medicine cabinet 62. Second inspection unit 65 certifies that second inspector 77 has performed a second inspection at medicine cabinet 62.

In the case where second inspector 77 is a different person from first inspector 12, inspector check unit 21 permits second inspection unit 65 to certify completion of the inspection. A series of medicine preparations performed in different locations is inspected by different first and second inspectors 12 and 77, thereby achieving reliable medicine preparation.

First person-authentication unit 32 identifies first preliminary inspector 11. Medicine shelf 16 includes first preliminary inspection unit 35, which certifies that first preliminary inspector 11 has performed a first preliminary inspection at medicine shelf 16. Inspector check unit 21 permits first inspection unit 36 to certify completion of the inspection when first inspector 12 has been determined to be a different person from first preliminary inspector 11. Thus, the inspection at medicine shelf 16 is performed by two persons, thereby providing reliable medicine preparation.

Second person-authentication unit 64 identifies second preliminary inspector 76. Medicine cabinet 62 includes second preliminary inspection unit 68, which certifies that second preliminary inspector 76 has performed a preliminary inspection at medicine cabinet 62. Inspector check unit 21 permits second inspection unit 65 to certify completion of the inspection when second inspector 77 has been determined to be a different person from second preliminary inspector 76. Thus, the inspection at medicine cabinet 62 is also performed by two persons, thereby providing reliable medicine preparation.

The following is a detailed description of each component of medicine cabinet 62. Medicine cabinet 62 includes second display unit 63, second person-authentication unit 64, and second inspection unit 65. Second display unit 63 displays the names of medicines to be arranged in transfer container 13. Second person-authentication unit 64 identifies second inspector 77 who inspects second medicines. Second inspection unit 65 certifies that second inspector 77 has performed a second inspection of the medicines arranged in transfer container 13.

Medicine cabinet 62 contains infusion bags and other medicines that cannot be kept in medicine shelf 16 because of needing to be kept under controlled temperature, being too large in size, or other reasons. Medicine cabinet 62 further contains dangerous medicines which should be kept more carefully than those contained in medicine shelf 16.

The "second medicines" indicate the medicines kept in medicine cabinet 62 of all medicines on a prescription. When second inspector 77 performs an inspection, second display unit 63 displays the names of all medicines on the prescription.

Medicine cabinet 62 further includes second ID-number detection unit 66, medicine collection information detection unit 67, second preliminary inspection unit 68, and LAN connection unit 61. Second ID-number detection 66 detects the transfer container ID number of transfer container 13 from bar-code tag 17. Medicine collection information detection unit 67 detects, from the bar code on transfer container 13, the medicines to be arranged from medicine cabinet 62. Second preliminary inspection unit 68 certifies that second preliminary inspector 76 has performed a preliminary inspection. LAN connection unit 61 performs transmission and reception of information.

At least one of first and second person-authentication units 32 and 64 has a biometric authentication function to perform person authentication using a fingerprint, facial features, a vein pattern, an iris pattern, or the like.

Thus, medicine arrangement in transfer container 13 is inspected by different first and second inspectors 12 and 77, thereby providing a reliable inspection.

Figure 15:
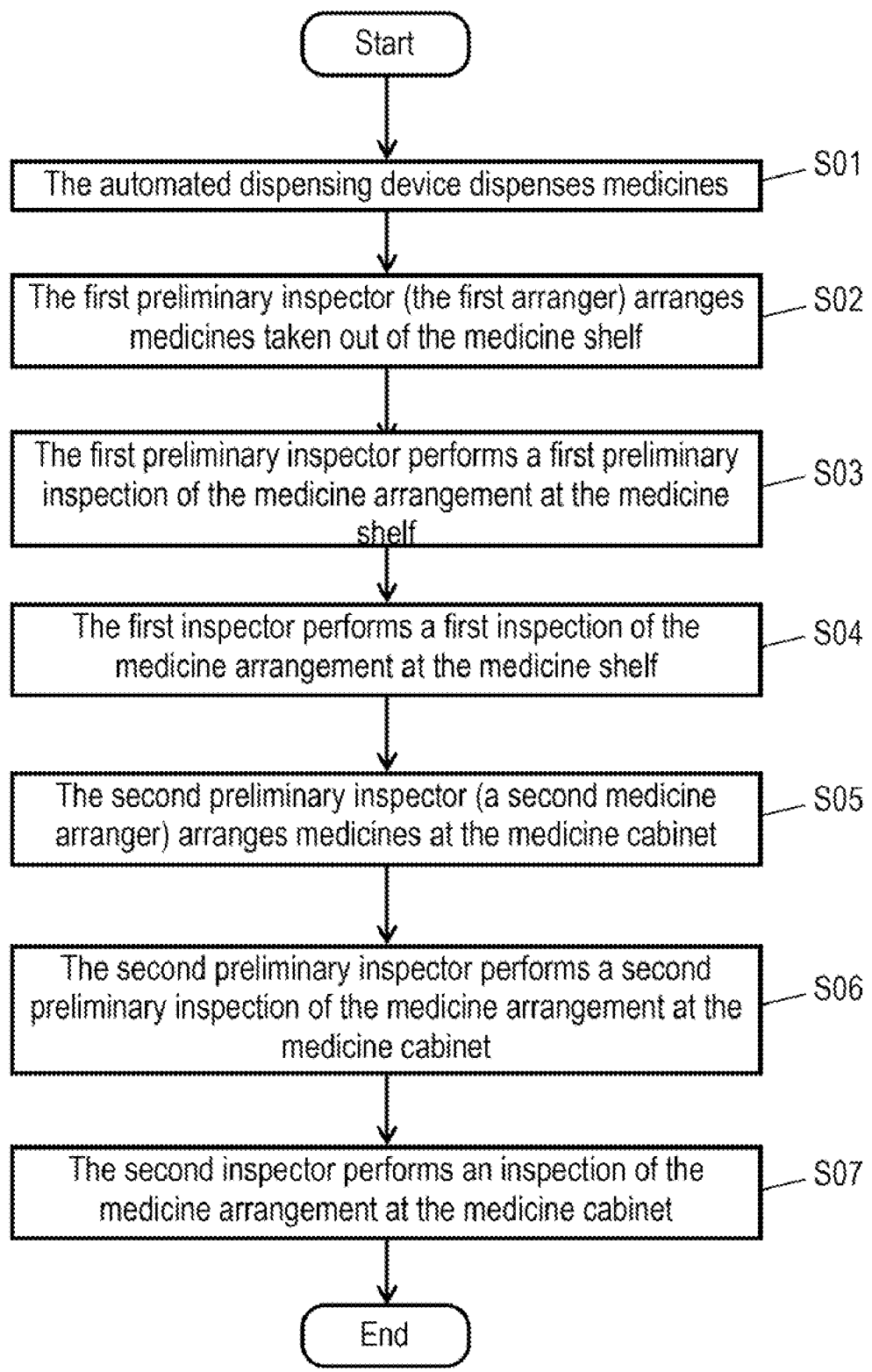
FIG. 15 is a flowchart of a medicine inspection support process according to the fourth embodiment of the invention.

FIG. 15 is a flowchart of a medicine inspection support process at medicine shelf 16 and medicine cabinet 62. A medicine inspection procedure according to medicine inspection support system 60 of the present first embodiment will be described as follows.

First of all, upon receiving prescription information, automated dispensing device 15 dispenses medicines into transfer container 13 according to the prescription information (Step S01).

Transfer container 13 containing the medicines dispensed from automated dispensing device 15 is transferred to medicine shelf 16. Then, a first medicine-arranger having a pharmacist license takes necessary medicines out of medicine storage compartments 25 of medicine shelf 16 into transfer container 13 (Step S02).

When the medicine arrangement in transfer container 13 is completed, the first medicine-arranger performs a preliminary inspection to confirm that the medicine arrangement has been done correctly (Step S03). When there is no problem, first preliminary inspection unit 35 certifies that the first medicine-arranger has performed the first preliminary inspection. The certification is achieved by the first medicine-arranger touching the letter "Confirmed" shown on first display unit 31.

Having completing the first preliminary inspection, the first medicine-arranger informs first inspector 12 of its completion. Next, first inspector 12 performs a first inspection of medicines arranged in transfer container 13 (Step S04).

As described above, Steps S01, S02, S03, and S04 are the same as those in the first embodiment. Transfer container 13 which has gone through the first inspection is transferred to medicine cabinet 62. Next, a second medicine arranger takes necessary medicines out of medicine cabinet 62 into transfer container 13 (Step S05).

Second preliminary inspector 76, who is the second medicine arranger, performs a second preliminary inspection of medicine arrangement (Step S06). Then, second preliminary inspector 76 informs second inspector 77 of the completion of the second preliminary inspection. Second inspector 77 performs an inspection of all medicines arranged in transfer container 13 (Step S07).

In this manner, the medicine preparation is performed according to the medicine inspection support system in which first and second inspectors 12 and 77 are made different persons.

The following is a detailed description of the medicine arrangement in Step S05 and the second preliminary inspection in Step S06 shown in the flowchart of FIG. 15.

Figure 16:
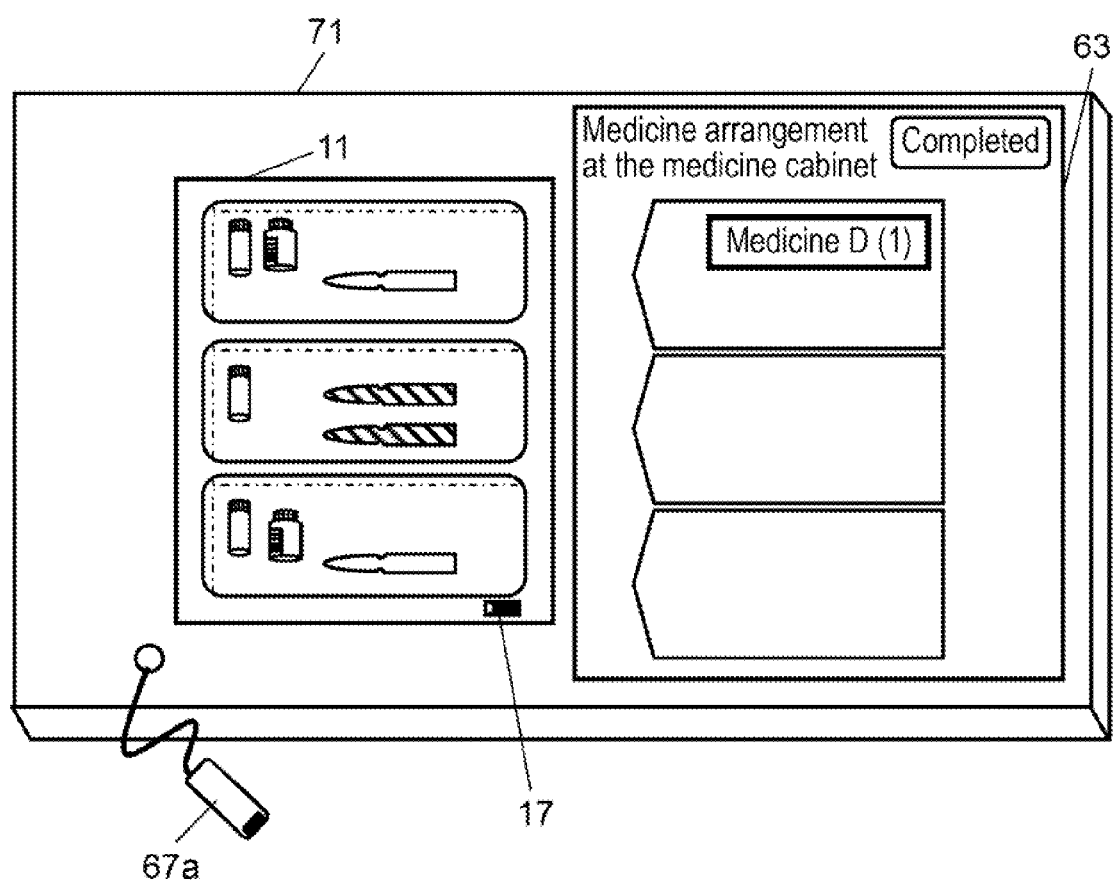
FIG. 16 is an overhead view of the workbench of a medicine cabinet on which a second inspection is performed according to the fourth embodiment of the invention.

FIG. 16 is an overhead view of workbench 71 of medicine cabinet 62 while medicines are being arranged. Workbench 71 includes second display unit 63, which is a touch monitor. Transfer container 13 is put on the space provided therefor adjacent to second display unit 63.

Figure 17:
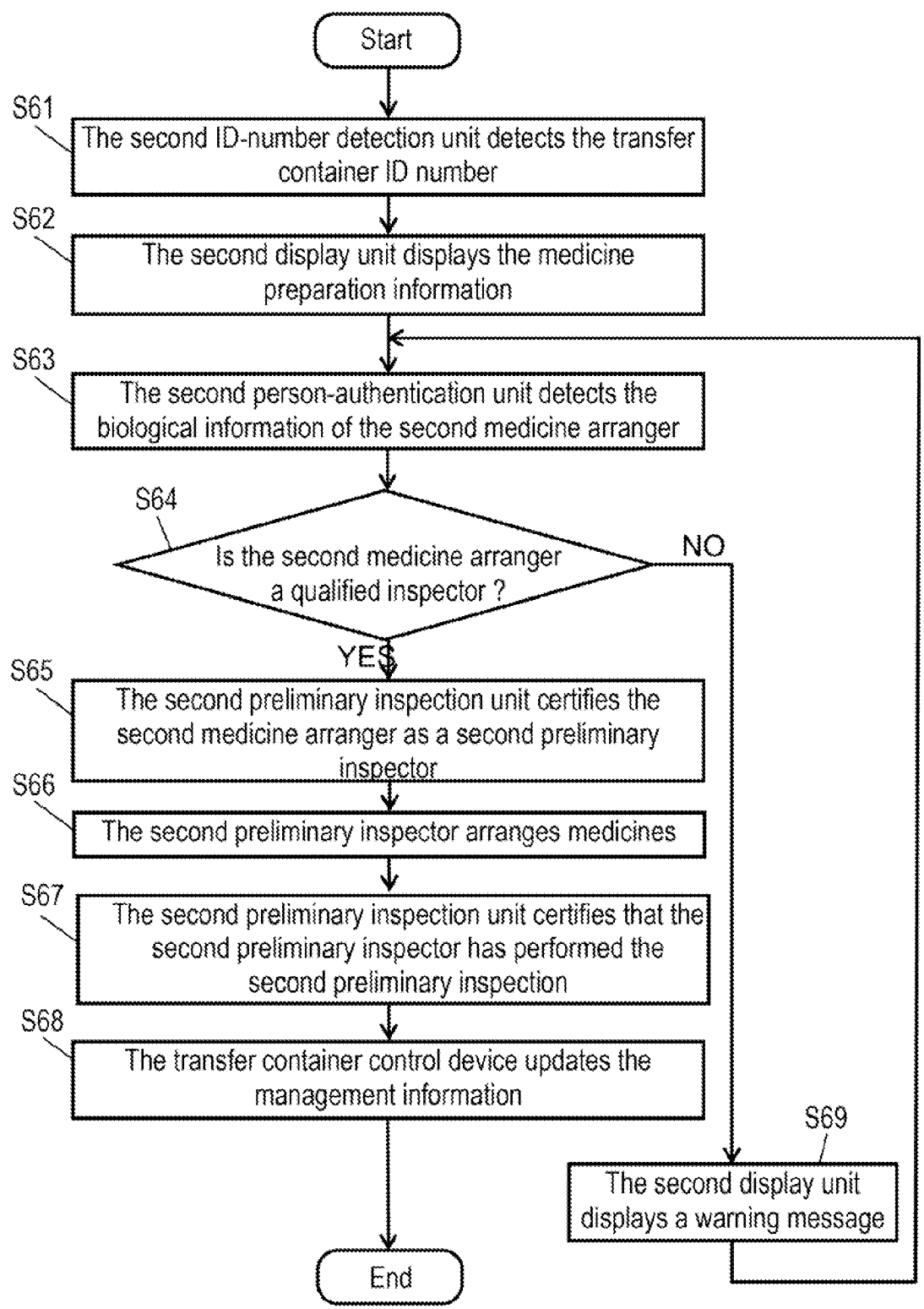
FIG. 17 is a flowchart of medicine arrangement and a second preliminary inspection according to the fourth embodiment of the invention.

FIG. 17 is a flowchart of the medicine arrangement and the second preliminary inspection at medicine cabinet 62. First of all, a second medicine-arranger scans bar-code tag 17 of transfer container 13 put on the space provided therefor with bar-code reader 67a so that the transfer container ID number is detected (Step S61). Bar-code reader 67a is the mouth of second ID-number detection unit 66. The detection of the transfer container ID number is performed by unit 66. The detected ID number is transferred to transfer container information recording unit 20 of transfer container control device 14.

FIG. 18 shows transfer container management table 72. Table 72 recorded in transfer container information recording unit 20 is compared with the transfer container ID number detected by second ID-number detection unit 66. The prescription information indicating the medicines to be arranged in transfer container 13 is transferred to medicine cabinet 62. Second display unit 63 displays the second medicines to be arranged according to the prescription information.

As shown in FIG. 16, a medicine D, which is a second medicine displayed on second display unit 63, can be dispensed from medicine cabinet 62. While the second medicine is being arranged, second display unit 63 displays its name and number in correspondence with the respective areas of transfer container 13 (Step S62).

Then, the second medicine arranger uses second person-authentication unit 64 so as to be certified as second preliminary inspector 76 as follows. First of all, second person-authentication unit 64 detects the biological information of the second medicine arranger (Step S63). Unit 64 then makes an inquiry to personnel information management unit 22 about who is the second medicine arranger and whether he/she has a pharmacist license. In other words, unit 64 determines whether the second medicine arranger is a qualified inspector (Step S64).

When it has been determined that the second medicine arranger is registered in personnel information management unit 22 and has a pharmacist license, he/she is permitted to perform medicine arrangement.

Thus, second preliminary inspection unit 68 certifies the second medicine arranger 76 as second preliminary inspector 76 (Step S65).

In this manner, second preliminary inspector 76 is identified through Steps S63, S64, and S65.

The second medicine arranger, who has been permitted to perform medicine arrangement takes the medicine D out of medicine cabinet 62, scans its bar code with barcode reader 73, and puts the medicine D into transfer container 13 (Step S66).

After putting the medicine D into transfer container 13, the second medicine arranger performs a preliminary inspection to check whether the medicine arrangement has been done correctly. When the determination is affirmative, the second medicine arranger touches the letter "Confirmed" shown on second display unit 63, which is a touch monitor. As a result, second preliminary inspection unit 68 certifies that the second preliminary inspector has performed the second preliminary inspection (Step$_p$ S67).

After the second medicine arranger has been certified as second preliminary inspector 76, the following information is transferred to transfer container control device 14: the second preliminary inspector information obtained from second person-authentication unit 64, and the medicine collection information and the transfer container management number obtained by medicine collection information detection unit 67. These pieces of information are added to transfer container management table 72 stored in transfer container information recording unit 20. In other words, transfer container control device 14 updates the management information held in unit 20 (Step S68).

When the second medicine arranger has been determined not to be a qualified inspector in Step S64, second display unit 63 displays a message to this effect Having completed a second preliminary inspection, second preliminary inspector 76 calls second inspector 77, who performs an inspection of medicine arrangement in transfer container 13. The following is a detailed description of the second inspection in Step S07 of the flowchart of FIG. 15.

Figure 19:
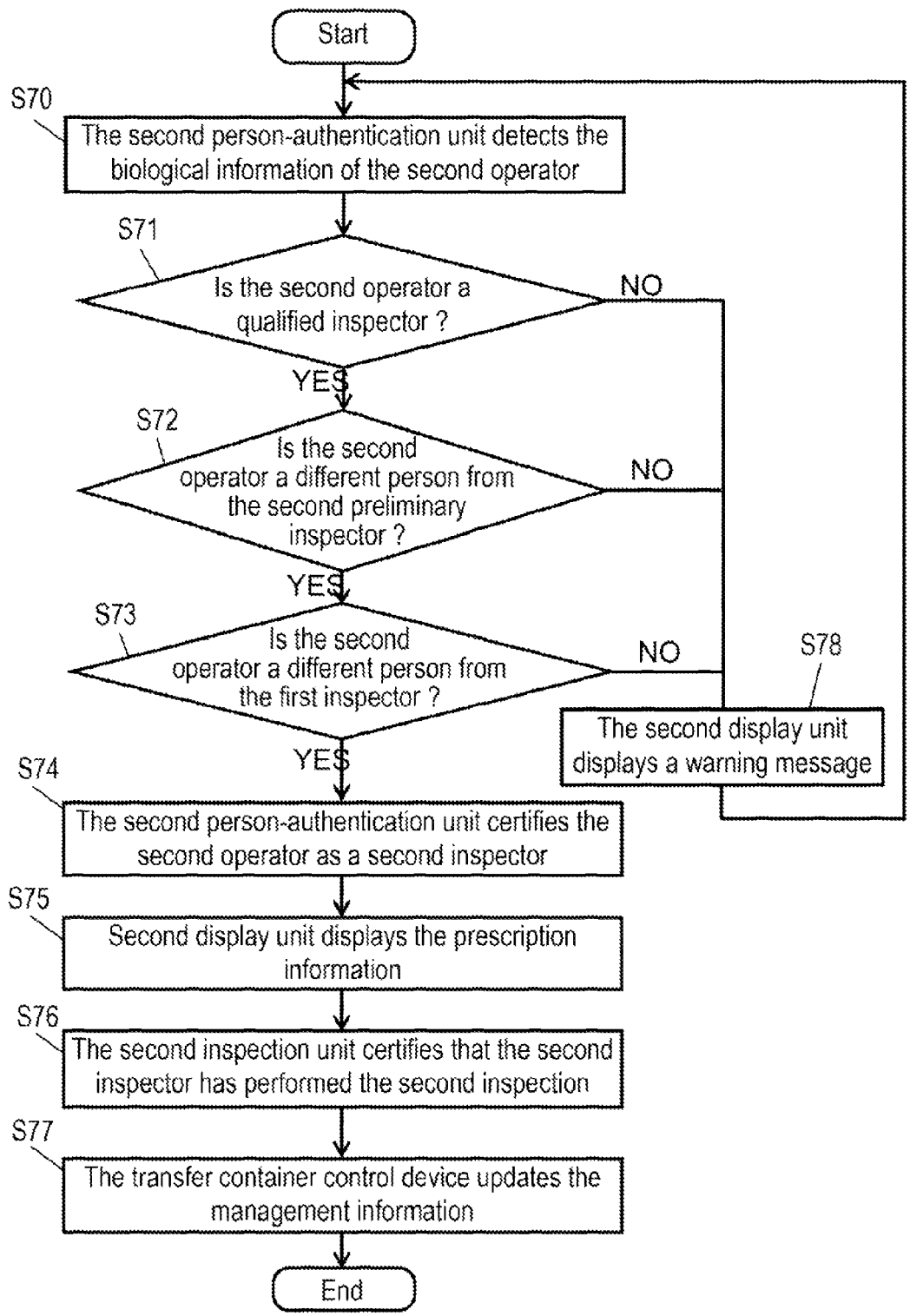
FIG. 19 is a flowchart of the second preliminary inspection according to the fourth embodiment of the invention.

FIG. 19 is a flowchart of a second inspection at medicine cabinet 62. A second operator uses second person-authentication unit 64 so as to be certified as second inspector 77 as follows. First of all, second person-authentication unit 64 detects the biological information of the second operator (Step S70).

The second operator is certified by second person-authentication unit 64 as follows. Second person-authentication unit 64 makes an inquiry to personnel information management unit 22 about who is the second operator and whether he/she has a pharmacist license. In other words, unit 64 determines whether the second operator is a qualified inspector (Step S71).

Inspector check unit 21 determines whether the second operator is a different person from second preliminary inspector 76, who is the second medicine-arranger (Step S72). When having determined that the second operator is a qualified inspector and is a different person from second preliminary inspector 76, inspector check unit 21 further determines whether the second operator is a different person from first inspector 12 (Step S73). Inspector check unit 21 then compares the information about the first inspector on transfer container management table 72 and the information about the second inspector identified by second person-authentication unit 64, thereby determining whether the second operator is a different person from first inspector 12.

When having determined that the second operator is a different person from first inspector 12, inspector check unit 21 permits the second inspector to perform an inspection. Then, second person-authentication unit 64 certifies the second operator as a second inspector (Step S74).

In this manner, the second inspector is identified through Steps S70, S71, S73, and S74.

In the case where the transfer container ID number detected by first ID-number detection unit 33 agrees with the transfer container ID number detected by second ID-number detection unit 66, when second inspector 77 is determined to be a different person from first inspector 12, the second inspection unit is permitted to certify completion of the inspection.

In other words, when transfer container 13 which has gone through the inspection at medicine shelf 16 is detected at medicine cabinet-62, it is determined whether the second operator is the same person as the first inspector.

Figure 20:
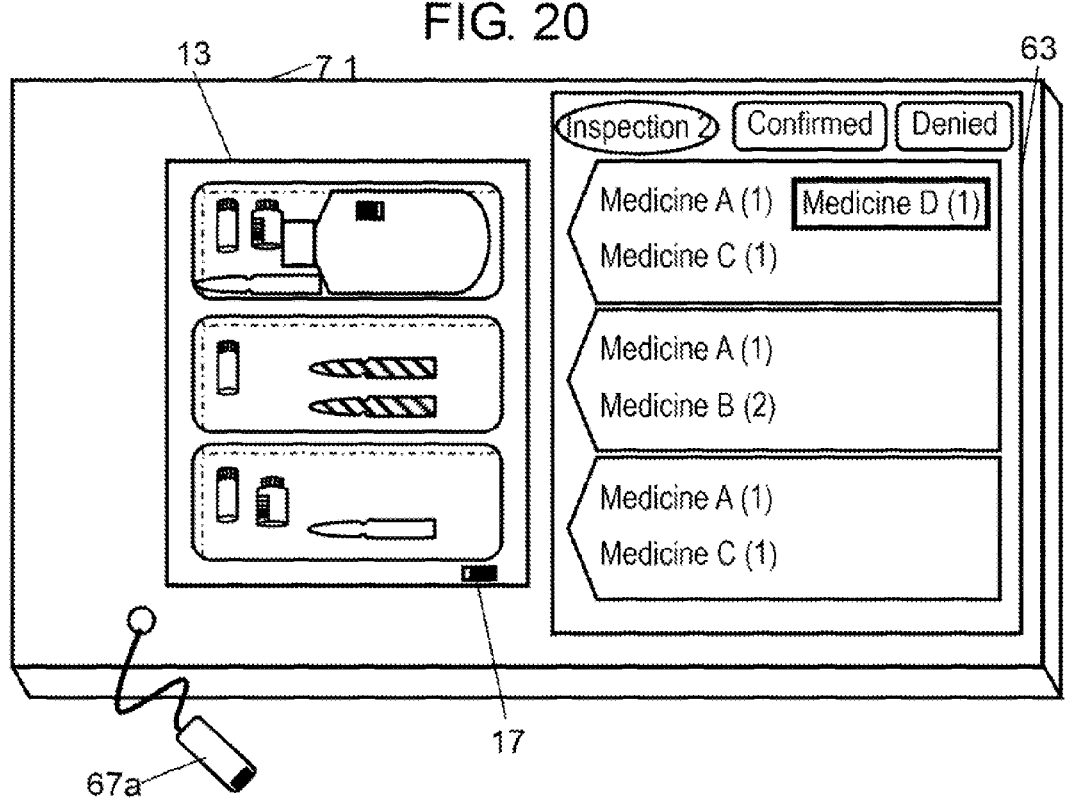
FIG. 20 is an overhead view of the workbench of the medicine cabinet on which another second inspection is performed according to the fourth embodiment of the invention.

FIG. 20 is an overhead view of workbench 18 of medicine cabinet 62 on which a second inspection is performed. Second display unit displays the name and the number of the second medicine to be put into transfer container 13 at medicine cabinet 62 more prominently than those of the other medicines contained in the prescription information in the same manner as in FIG. 6 (Step S75).

Second inspector 77 inspects as to whether the medicine arrangement in transfer container 13 has been done correctly by referring to the information displayed on second display unit 63. When the determination is affirmative, second inspector 77 touches the letter "Confirmed" shown on second display unit 63. As a result, second inspection unit 65 certifies that second inspector 77 has performed the second inspection (Step S76).

The information about the second inspector identified by second person-authentication unit 64 is transferred to transfer container control device 14, and added to transfer container management table 72 stored in transfer container information recording unit 20. In other words, transfer container control device 14 updates the management information held in unit 20 (Step S77).

When second inspector 77 has been determined to be the same person as first inspector 12 in Step S73, on the other hand, inspector check unit 21 does not permit second inspector 77 to perform a second inspection.

Figure 21:
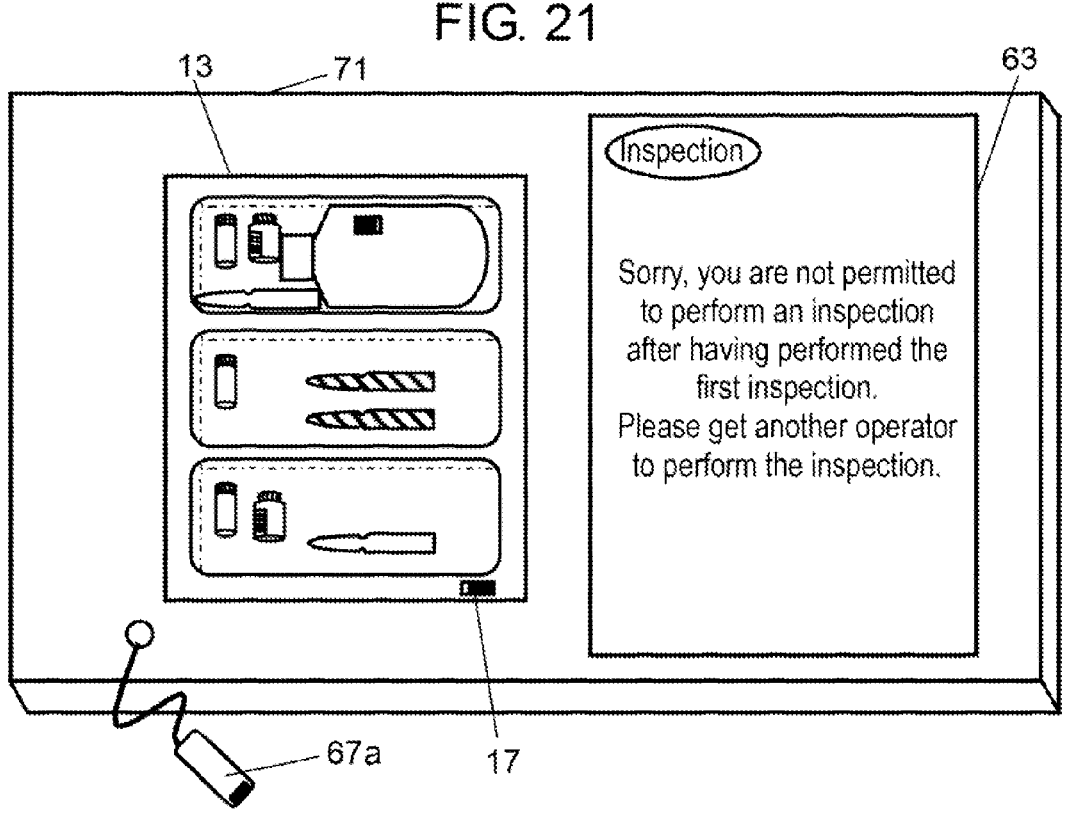
FIG. 21 is an overhead view of the workbench of the medicine cabinet when the first inspector and the second inspector are the same person according to the fourth embodiment of the invention.

FIG. 21 is an overhead view of the workbench of the medicine cabinet in the case where the first and second inspectors are the same person. As shown in FIG. 21, second display unit 63 displays a warning message indicating thk second inspector 77 is the same person as first inspector 12 (Step S78). Furthermore, second display unit 63 does not display the letter "Confirmed" so as to prevent the certification of the second inspection.

As described hereinbefore, the medicine inspection support system requires first inspector 12 inspecting at medicine shelf 16 and second inspector 77 inspecting at medicine cabinet 62 to be different persons, thereby providing highly reliable medicine arrangement.

In the above-described medicine inspection support system 60, inspector check unit 21 is included in transfer container control device 14, but may alternatively be included in medicine shelf 16 or in medicine cabinet 62.

Fifth Embodiment

The medicine inspection support system of a fifth embodiment of the invention includes a first medicine-preparation unit and a second medicine-preparation unit. The first medicine-preparation unit is where a first inspector performs a first inspection, and the second medicine-preparation unit is where a second inspector performs a second inspection. In the case where the second inspector is the same person as the first inspector, he/she is permitted to perform a second inspection, provided that the time elapsed since a first operation certification time has reached or exceeded a refresh time.

Figure 22:
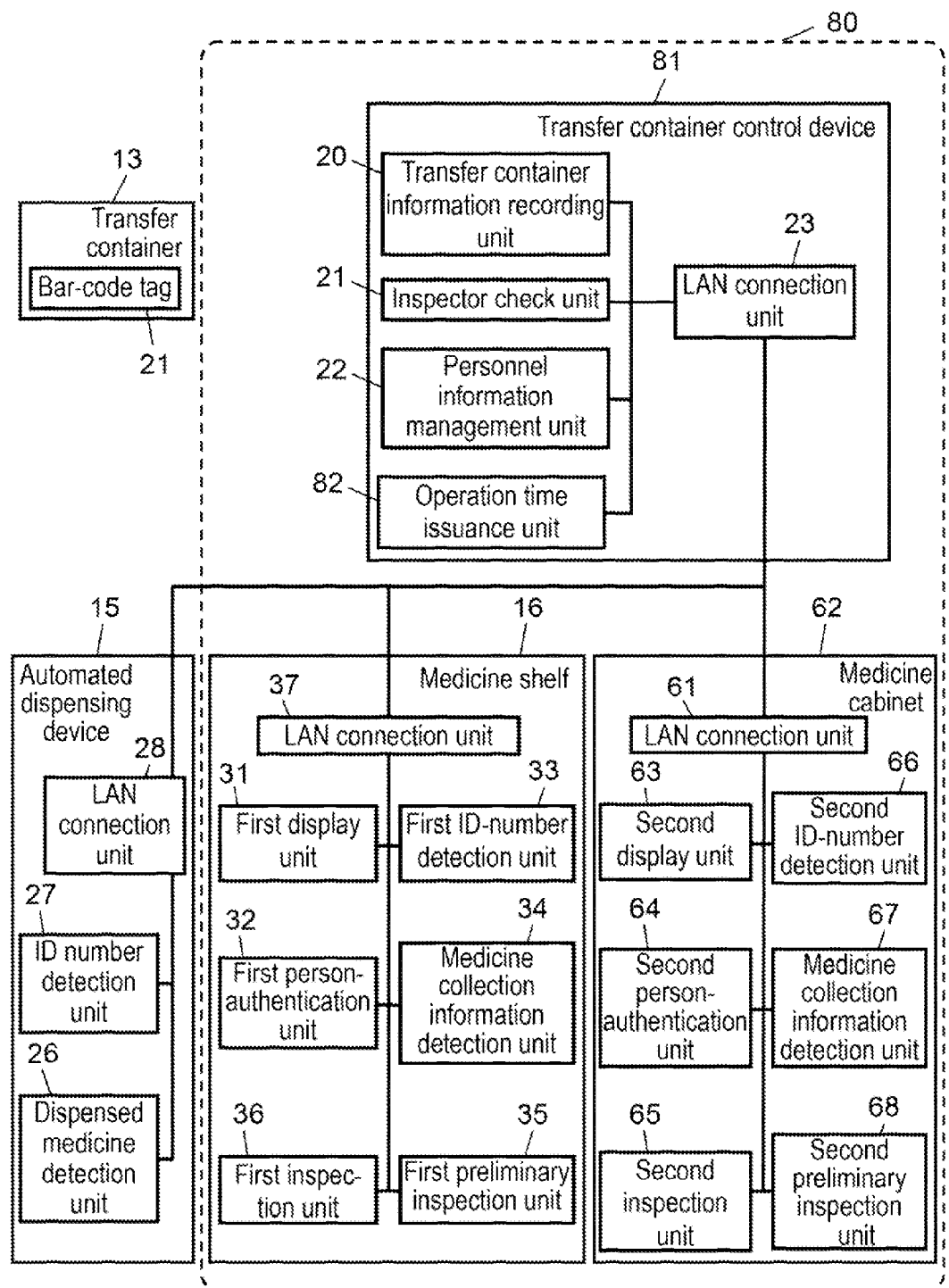
FIG. 22 is a block diagram of a medicine inspection support system according to a fifth embodiment of the invention.
Figure 24:
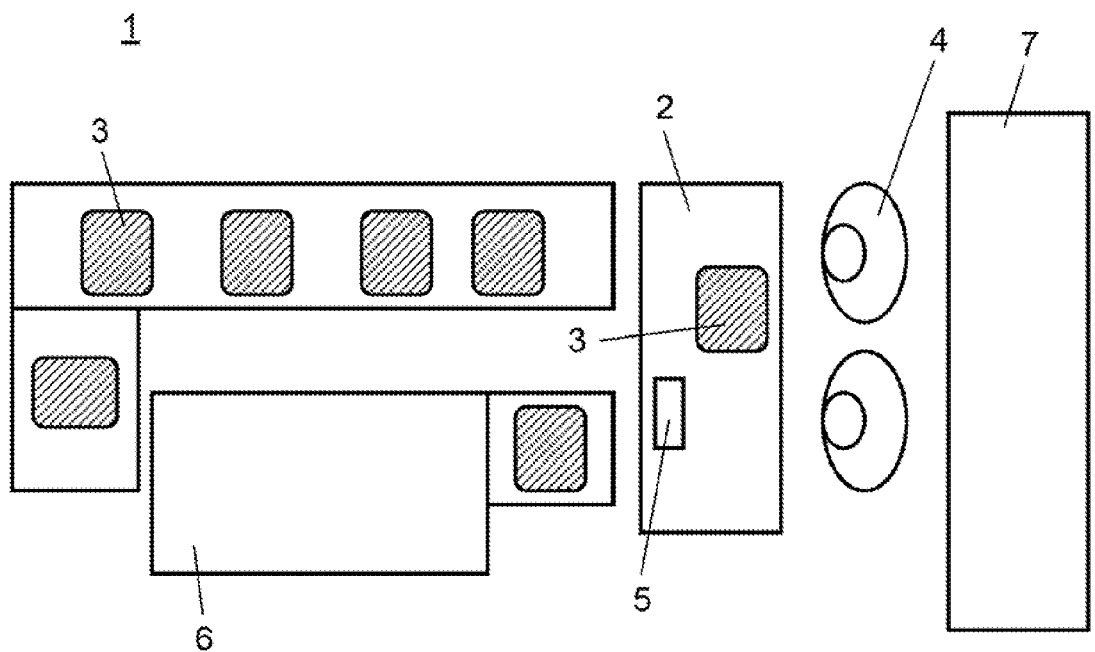
FIG. 24 is a schematic diagram of a conventional medicine inspection support system.

FIG. 22 is a block diagram of medicine inspection support system 80 of the fifth embodiment. As shown in FIG. 22, system 80 includes operation time issuance unit 82, which issues a first operation certification time and a second operation certification time. The first operation certification time is when first inspection unit 36 inspects medicine shelf 16, and the second operation certification time is when second inspector 77 is certified at medicine cabinet 62. Medicine shelf 16 is the first medicine-preparation unit, and medicine cabinet 62 is the second medicine-preparation unit.

Having determined that second inspector 77 is the same person as first inspector 12, inspector check unit 21 permits second inspection unit 65 to certify completion of the inspection when the time difference between the first and second operation certification times is not less than the refresh time.

The "refresh time" means the time required for an inspector to refresh and recover from the fatigue of an inspection that requires intense concentration. In the present embodiment, the refresh time is set to one hour which is generally considered to allow people to refresh and recover.

Medicine inspection support system 80 of the present fifth embodiment is obtained by adding operation time issuance unit 82 to medicine inspection support system 60 of the fourth embodiment.

In the case where second inspector 77 is the same person as first inspector 12, inspector check unit 21 permits a second inspection to be performed upon the satisfaction of the condition that the interval between the first and second operation certification times is not less than the refresh time. The first operation certification time is when first inspection unit 36 certifies an inspection of the first medicines, and the second operation certification time is when second person-authentication unit 64 identifies the second inspector.

Medicine inspection support system 80 of the present fifth embodiment includes transfer container control device 81, which includes transfer container information recording unit 20, inspector check unit 21, personnel information management unit 22, and LAN connection unit 23. Device 81 further includes operation time issuance unit 82, which issues the operation times.

An inspection procedure according to the present fifth embodiment will be described as follows. When first inspector 12, who is performing a first inspection of the medicines in transfer container 13 on workbench 18 of medicine shelf 16, determines that the medicine arrangement has been done correctly, first inspection unit 36 certifies the first inspection.

FIG. 23 shows a transfer container management table. The information about the first inspector is added to transfer container management table 74 shown in FIG. 23. At the same time, operation time issuance unit 82 issues the first operation certification time, which is also added to table 74.

Next, a second inspection is performed at medicine cabinet 62 as follows. The information about the first inspector contained in the same transfer container on transfer container management table 74 is extracted according to the transfer container ID number scanned with bar-code reader 67a. Then inspector check unit 21 compares the information about the first inspector contained in table 74 with the information about the second inspector obtained from second person-authentication unit 64 so as to determine whether first and second inspectors 12 and 77 are different persons.

In the case where first and second inspectors 12 and 77 are the same person, the first operation certification time is extracted from transfer container management table 74. Furthermore, inspector check unit 21 asks operation time issuance unit 82 to issue the current operation time, which is made the second operation certification time.

Inspector check unit 21 calculates whether the interval between the first and second operation certification times has passed the refresh time of one hour or more. When the interval has passed the refresh time, second inspector 77 is permitted to perform a second inspection. Second display unit 63 of medicine cabinet 62 displays the names and numbers of the medicines contained in the prescription information so that the second inspection can be performed.

If the interval has not passed the refresh time, on the other hand, second inspector 77 is not permitted to perform a second inspection.

Thus, a reliable inspection can be performed by a single inspector.

INDUSTRIAL APPLICABILITY

The medicine inspection support system of the invention, which provides reliable medicine preparation, is applicable to medicine-preparation unit used in hospitals, dispensing pharmacies, and other facilities.

REFERENCE MARKS IN THE DRAWINGS 10, 50, 60, 80 medicine inspection support system
11 first preliminary inspector
12 first inspector
13 transfer container
14, 52, 81 transfer container control device
15 automated dispensing device
16 medicine shelf
17 bar-code tag
18, 71 workbench
20 transfer container information recording unit
21 inspector check unit
22 personnel information management unit
23, 28, 37, 61 LAN connection unit
24, 41, 73, 67a bar-code reader
25 medicine storage compartment
26 dispensed medicine detection unit
27 ID number detection unit
29, 72, 74 transfer container management table
31 first display unit
32 first person-authentication unit
33 first ID-number detection unit
34, 67 medicine collection information detection unit
35 first preliminary inspection unit 36 first inspection unit
51, 82 operation time issuance unit
62 medicine cabinet
63 second display unit
64 second person-authentication unit
65 second inspection unit
66 second ID-number detection unit
68 second preliminary inspection unit
76 second preliminary inspector
77 second inspector

The invention claimed is:

1. A medicine inspection support system for certifying that medicine preparation has been inspected by an inspection unit, the system comprising:
 a person authentication unit for identifying a preliminary inspector who performs a preliminary inspection of the medicine preparation, and an inspector who performs an inspection of the medicine preparation;
 a preliminary inspection unit for certifying that the preliminary inspector has performed the preliminary inspection of the medicine preparation;
 the inspection unit for certifying that the inspector has performed the inspection of the medicine preparation;
 an inspector check unit for permitting the inspection unit to certify completion of the inspection when determined that the inspector is a different person from the preliminary inspector; and
 an operating information issuance unit for issuing a first operation certification time and a second operation certification time, the first operation certification time being when the preliminary inspection unit certifies the preliminary inspection of the medicine preparation, and the second operation certification time being when the inspector is identified, wherein
 in a case of having determined that the inspector is the same person as the preliminary inspector, the inspector check unit permits the inspection unit to certify completion of the inspection when a time difference between the first operation certification time and the second operation certification time is not less than a predetermined time.

2. The medicine inspection support system of claim 1, wherein
 in the case of having determined that the inspector is the same person as the preliminary inspector, the inspector check unit permits the inspect unit to certify completion of the inspection when the time difference between the first operation certification time and the second operation certification time is not less than a refresh time.

3. The medicine inspection support system of claim 1, wherein the person authentication unit has a biometric authentication function.

4. The medicine inspection support system of claim 3, wherein
 the biometric authentication function is an iris recognition function.

5. The medicine inspection support system of claim 1, wherein
 the medicine preparation is to arrange medicines in a transfer container.

6. The medicine inspection support system of claim 1, wherein
 the medicine preparation is to mix a plurality of medicines.

7. A medicine inspection support system comprising:
 a first medicine-preparation unit where first medicine-preparation is performed,
 a second medicine-preparation unit where second medicine-preparation is performed, the first medicine-preparation unit including:
  a first person-authentication unit for identifying a first inspector who performs an inspection at the first medicine-preparation unit; and
  a first inspection unit for certifying that the first inspector has performed the inspection at the first medicine-preparation unit;
 the second medicine-preparation unit including:
  a second person-authentication unit for identifying a second inspector who performs an inspect at the second medicine-preparation unit; and
  a second inspection unit for certifying that the second inspector has performed the inspect at the second medicine-preparation unit;
 an inspector check unit for permitting the second inspection unit to certify completion of the inspection when determined that the second inspector is a different person from the first inspector;
 an operation time issuance unit for issuing a first operation certification time and a second operation certification time, the first operation certification time being when the first inspection unit performs an inspection of the first medicine-preparation, and the second operation certification time being when the second inspector is identified at the second medicine-preparation unit, wherein
 in a case of having determined that the second inspector is the same person as the first inspector, the inspector check unit permits the second inspection unit to certify completion of the inspection when a time difference between the first operation certification time and the second operation certification time is not less than a predetermined time.

8. The medicine inspection support system of claim 7, wherein
 in the case of having determined that the second inspector is the same person as the first inspector, the inspector check unit permits the second inspection unit to certify completion of the inspection when the time difference between the first operation certification time and the second operation certification time is not less than a refresh time.

9. The medicine inspection support system of claim 7, wherein
 the first medicine-preparation unit includes a first ID-number detection unit for detecting a transfer container ID number from an identification tag of a transfer container;
 the second medicine-preparation unit includes a second ID-number detection unit for detecting a transfer container ID number from an identification tag of a transfer container; and
 in a case where the transfer container ID number detected by the first ID-number detection unit is identical to the transfer container ID number detected by the second ID-number detection unit, the inspector check unit permits the second inspection unit to certify completion of the inspection when the second inspector has been determined to be a different person from the first inspector.

10. The medicine inspection support system of claim 7, wherein
 the first person-authentication unit identifies the first preliminary inspector;
 the first medicine-preparation unit includes a first preliminary inspection unit for certifying that the first preliminary inspector has performed a preliminary inspection at the first medicine-preparation unit; and the inspector check unit permits the first inspection unit to certify completion of the inspection when determined that the first inspector is a different person from the first preliminary inspector.

11. The medicine inspection support system of claim 7, wherein
the second person-authentication unit identifies the second preliminary inspector;
the second medicine-preparation unit includes a second preliminary inspection unit for certifying that the second preliminary inspector has performed a preliminary inspection at the second medicine-preparation unit; and
the inspector check unit permits the first inspection unit to certify completion of the inspection when determined that the second inspector is a different person from the second preliminary inspector.

12. The medicine inspection support system of claim 7, wherein
the first medicine-preparation unit is a medicine shelf having a medicine storage compartment for storing the first medicine; and
the second medicine-preparation unit is a medicine cabinet having a medicine storage compartment for storing the second medicine.

13. The medicine inspection support system of claim 7, wherein
at least one of the first person-authentication unit and the second person-authentication unit has a biometric authentication function.

* * * * *